(12) United States Patent
Takada et al.

(10) Patent No.: US 10,856,820 B2
(45) Date of Patent: Dec. 8, 2020

(54) AUXILIARY INSTRUMENT AND THREE-DIMENSIONAL IMAGE DATA CREATION METHOD USING AUXILIARY INSTRUMENT

(71) Applicant: KABUSHIKI KAISHA SHOFU, Kyoto (JP)

(72) Inventors: Hajime Takada, Kyoto (JP); Ryohei Kondo, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 0 days.

(21) Appl. No.: 16/366,077

(22) Filed: Mar. 27, 2019

(65) Prior Publication Data

US 2019/0298280 A1    Oct. 3, 2019

(30) Foreign Application Priority Data

Mar. 28, 2018  (JP) ................. 2018-061271

(51) Int. Cl.
*H05G 1/28* (2006.01)
*A61B 6/08* (2006.01)
(Continued)

(52) U.S. Cl.
CPC ............ *A61B 6/145* (2013.01); *A61B 6/52* (2013.01); *A61C 9/0053* (2013.01); *G06T 19/20* (2013.01);
(Continued)

(58) Field of Classification Search
CPC .......... A61B 1/0002; A61B 1/00057; A61B 1/00059; A61B 5/1077; A61B 5/4547;
(Continued)

(56) References Cited

U.S. PATENT DOCUMENTS 7,234,937 B2 *  6/2007  Sachdeva ................. A61C 7/00
                                                            433/24
8,821,158 B1 *  9/2014  Hultgren ............... A61C 9/0053
                                                            433/29

(Continued)

FOREIGN PATENT DOCUMENTS

| JP | 2009-233294 | 10/2009 |
|----|-------------|---------|
| KR | 10-1758801  | 7/2017  |
| WO | 2017/137398 | 8/2017  |

OTHER PUBLICATIONS

Communication pursuant to Article 94(3) EPC dated May 7, 2020 in corresponding European Patent Application No. 19 165 202.3.
(Continued)

*Primary Examiner* — Irakli Kiknadze
(74) *Attorney, Agent, or Firm* — Wenderoth, Lind & Ponack, L.L.P.

(57) ABSTRACT

An auxiliary instrument according to the present invention is an auxiliary instrument for dental use used as a reference of alignment for creating three-dimensional intraoral image data by connecting a plurality of pieces of three-dimensional image data obtained by three-dimensionally measuring an inside of an oral cavity, the auxiliary instrument including a sheet portion having a first surface and a second surface opposed to the first surface, and a plurality of identification portions formed in a thickness direction (Z direction) of the sheet portion from the first surface of the sheet portion, each of the plurality of identification portions having a three-dimensional shape configured to be identified.

9 Claims, 18 Drawing Sheets

(51) Int. Cl.
*A61B 6/14* (2006.01)
*A61B 6/00* (2006.01)
*A61C 9/00* (2006.01)
*G06T 19/20* (2011.01)
*A61B 90/00* (2016.01)

(52) U.S. Cl.
CPC ....... *A61B 2090/3966* (2016.02); *A61C 9/006* (2013.01); *A61C 9/0066* (2013.01); *A61C 9/0073* (2013.01); *A61C 2201/005* (2013.01)

(58) Field of Classification Search
CPC ... A61B 2090/3966; A61B 6/145; A61B 6/52; A61B 6/14; A61B 34/20; A61B 6/025; A61B 6/547; A61B 6/583; A61B 1/24; A61B 1/00147; A61B 2090/3983; A61B 2576/02; A61B 5/0077; A61B 5/0088; A61B 5/055; A61B 5/1072; A61B 6/027; A61B 6/032; A61B 6/035; A61B 6/0492; A61B 6/12; A61B 6/4423; A61B 6/469; A61B 6/505; A61B 6/508; A61B 5/4552; A61B 6/5241; A61B 5/7264; A61B 6/466; A61B 6/4085; A61B 6/4441; A61B 6/5205; G06T 2207/10028; G06T 19/20; G06T 15/30; G06T 17/20; G06T 2207/10116; G06T 2207/30036; G06T 2210/21; G06T 2210/41; G06T 2219/2004; G06T 7/55; G06T 7/579; G06T 7/97; G06T 2207/30008; G06T 7/344; G06T 7/11; G06T 19/006; G06T 2207/10081; G06T 7/0012; G06T 17/00; G06T 5/003; G06T 11/005; G06T 11/008; G06T 19/00; G06T 2219/2016; H04N 13/246; A61C 2201/005; A61C 9/0053; A61C 9/006; A61C 9/0066; A61C 9/0073; G01N 2223/6123; G01N 23/046; G01T 1/247; H01J 35/30; H05G 1/66
USPC ......... 378/4, 19, 162, 38, 39, 165, 168, 191, 378/205
See application file for complete search history.

(56) References Cited

U.S. PATENT DOCUMENTS

| | | | |
|---|---|---|---|
| 9,453,722 B2* | 9/2016 | Ertl | ........................... A61C 9/00 |
| 2012/0046668 A1* | 2/2012 | Gantes | ................... A61C 1/084 |
| | | | 606/130 |
| 2012/0046914 A1* | 2/2012 | Gao | ....................... A61C 1/084 |
| | | | 703/1 |
| 2012/0224756 A1* | 9/2012 | Ertl | ..................... A61C 9/0053 |
| | | | 382/131 |
| 2015/0209118 A1 | 7/2015 | Kopelmart et al. | |

OTHER PUBLICATIONS

Extended European Search Report dated Aug. 30, 2019 in European Application No. 19165202.3.

* cited by examiner

Fig.1
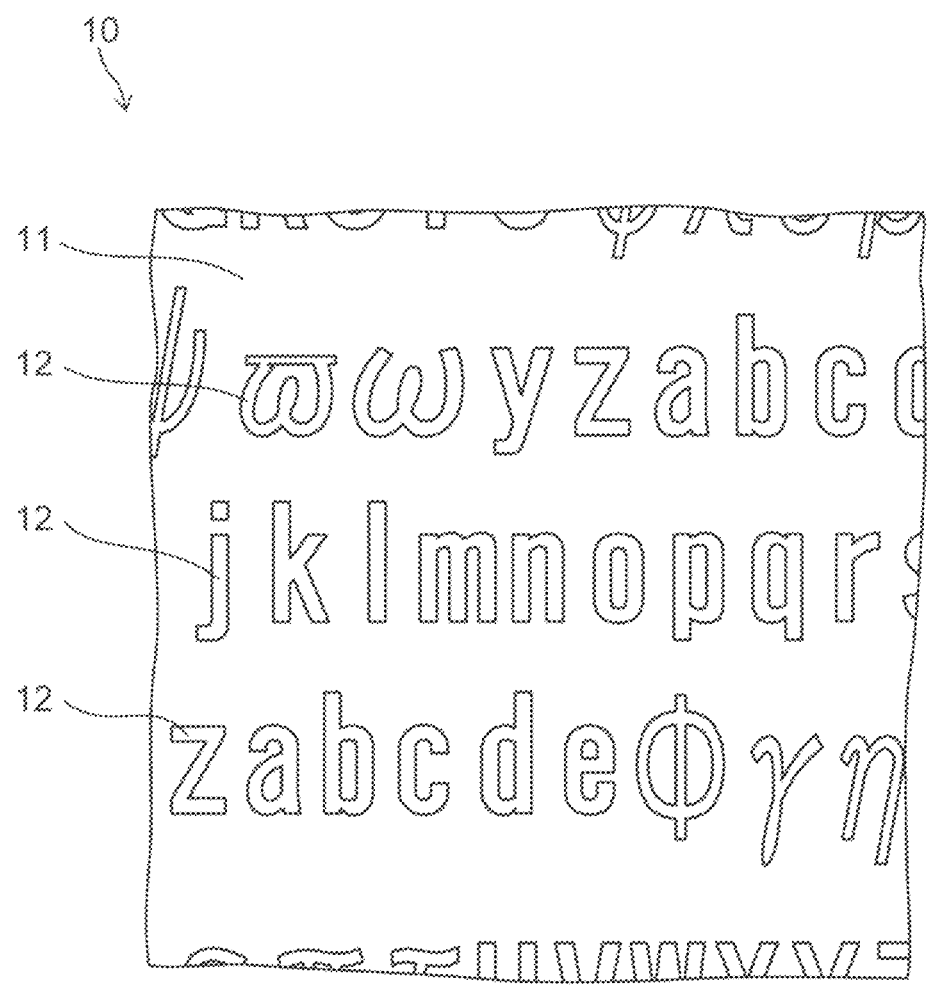
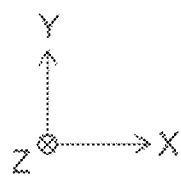

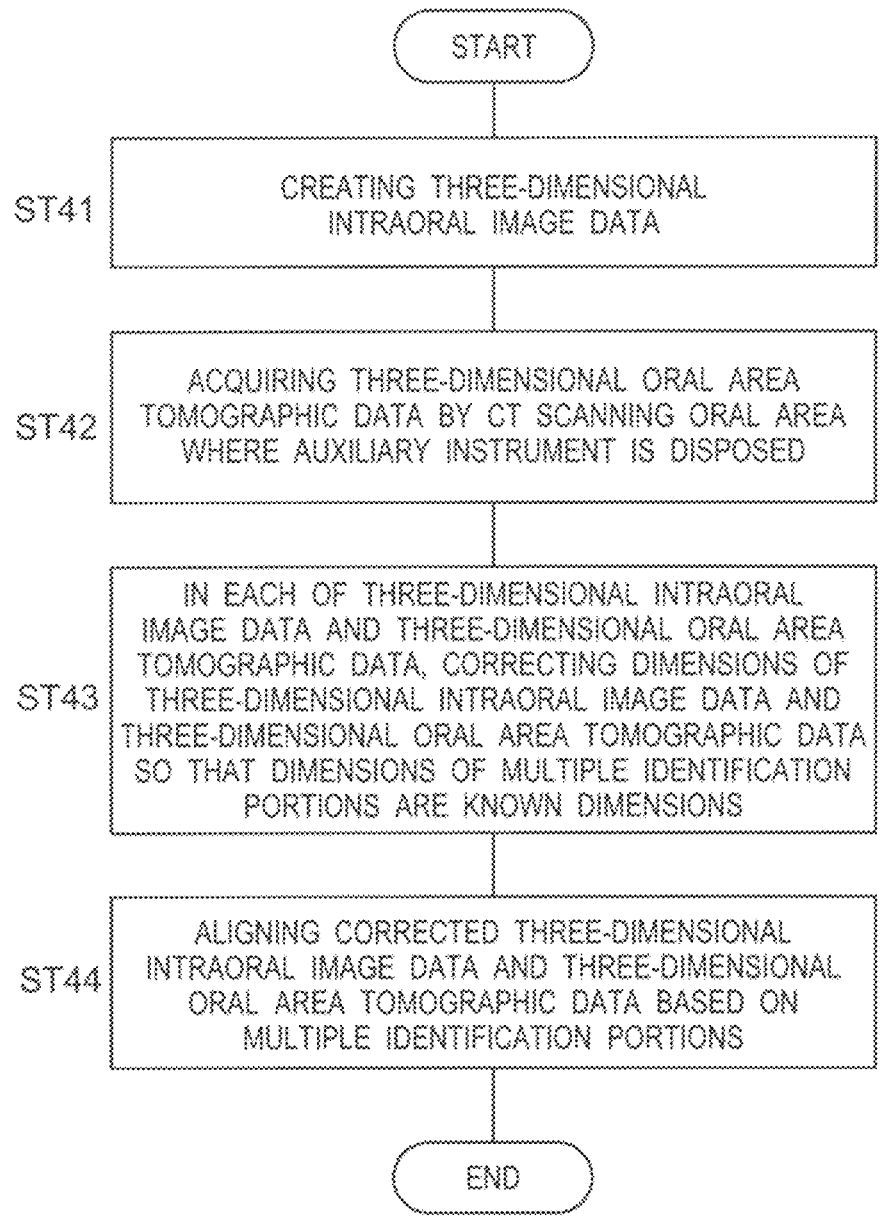

AUXILIARY INSTRUMENT AND THREE-DIMENSIONAL IMAGE DATA CREATION METHOD USING AUXILIARY INSTRUMENT

BACKGROUND OF THE INVENTION

Field of the Invention

The present invention relates to an auxiliary instrument and a three-dimensional image data creation method using an auxiliary instrument. In particular, the present invention relates to an auxiliary instrument which is disposed in an oral cavity when the inside of an oral cavity is three-dimensionally measured and which is used as a reference of alignment for creating three-dimensional intraoral image data by connecting a plurality of pieces of three-dimensional image data measured three-dimensionally, and a three-dimensional image data creation method using the auxiliary instrument.

Description of the Related Art

A marker for creating a three-dimensional tomographic image from three-dimensional oral area tomographic data of a patient's oral area and shape data of a patient's dentition model, and a creation method of a three-dimensional tomographic image using the marker are known (see, for example, Patent Document 1).

In the creation method of a three-dimensional tomographic image described in Patent Document 1, a marker is disposed in the oral area of a patient, and three-dimensional oral area tomographic data and three-dimensional image data of a dentition model are acquired. Then, in the creation method of a three-dimensional tomographic image in JP 2009-233294 A, aligning the three-dimensional oral area tomographic data and the three-dimensional image data of the dentition model with the position of the marker as a reference creates a three-dimensional tomographic image in which the two pieces of data are aligned.

In addition, in recent years, a method of creating three-dimensional intraoral image data by connecting a plurality of pieces of three-dimensional image data obtained by three-dimensionally measuring the inside of an oral cavity is known.

PRIOR ART DOCUMENT

Patent Document

Patent Document 1: Japanese Patent Publication No. 2009-233294A

SUMMARY OF THE INVENTION

It is required to improve precision and accuracy of three-dimensional intraoral image data in a method of creating three-dimensional intraoral image data by connecting a plurality of pieces of three-dimensional image data obtained by three-dimensionally measuring the inside of an oral cavity.

In order to solve the above problem, the present invention has an object to provide an auxiliary instrument capable of improving precision and accuracy of three-dimensional image data, and a three-dimensional image data creation method using the auxiliary instrument.

An auxiliary instrument according to one aspect of the present invention is an auxiliary instrument for dental use used as a reference of alignment for creating three-dimensional intraoral image data by connecting a plurality of pieces of three-dimensional image data obtained by three-dimensionally measuring an inside of an oral cavity, the auxiliary instrument including: a sheet portion having a first surface and a second surface opposed to the first surface; and a plurality of identification portions formed in a thickness direction of the sheet portion from the first surface of the sheet portion, each of the plurality of identification portions having a three-dimensional shape configured to be identified.

A three-dimensional image data creation method according to one aspect of the present invention is a three-dimensional image data creation method for creating image data inside a three-dimensional oral cavity by using an auxiliary instrument for dental use, the three-dimensional image data creation method including: while including an overlapping portion, three-dimensionally measuring an oral area in which an auxiliary instrument is disposed to acquire a plurality of pieces of three-dimensional image data obtained by three-dimensionally measuring both the auxiliary instrument and a shape in an oral cavity, the auxiliary instrument including: a sheet portion, and a plurality of identification portions formed in a thickness direction of the sheet portion from the first surface of the sheet portion, each of the plurality of identification portions having a three-dimensional shape configured to be identified; identifying each shape of the plurality of identification portions of the auxiliary instrument in each of the plurality of pieces of three-dimensional image data; identifying one or a plurality of identification portions the shape of which is similar in the overlapping portion between the plurality of pieces of three-dimensional image data; aligning the plurality of pieces of three-dimensional image data by using the identified one or a plurality of identification portions as a reference of alignment; and connecting the aligned plurality of pieces of three-dimensional image data to create three-dimensional intraoral image data.

According to the auxiliary instrument of the present invention and the three-dimensional image data creation method using the auxiliary instrument, precision and accuracy of three-dimensional intraoral image data can be improved.

BRIEF DESCRIPTION OF THE DRAWINGS

FIG. 1 is a schematic diagram illustrating an example of an auxiliary instrument according to a first embodiment of the present invention;

FIG. 12 is a flowchart of an example of a method of aligning three-dimensional oral area tomographic data and three-dimensional intraoral image data using the auxiliary instrument according to the first embodiment of the present invention;

Figure 2:
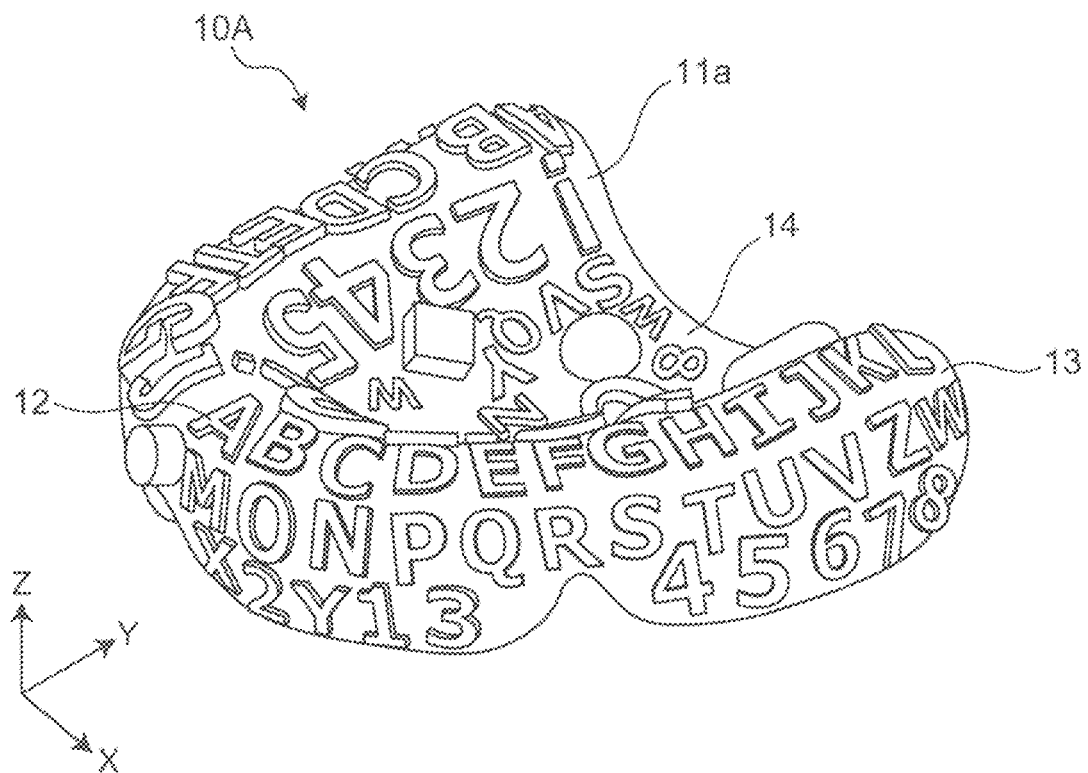
FIG. 2 is a schematic diagram illustrating an auxiliary instrument of a modified example according to the first embodiment of the present invention.

DESCRIPTION OF THE PREFERRED EMBODIMENT (Circumstances That Led to Present Invention) In clinical dentistry, dental professionals make models of patient's teeth, mucosae and abutment teeth to obtain information on the intraoral shape of a patient. For example, dental professionals make molds of patient's teeth, mucosae, and abutment teeth with an alginate impression material or a silicone impression material (hereinafter referred to as "impression taking"). Next, the dental professionals inject gypsum into the manufactured mold and harden it to manufacture models such as teeth, mucosae, and abutment teeth.

In such an impression taking method, there is a problem that patients experience pain such as vomiting reflex, thermal stimulation, and waiting curing of the impression material while opening the mouth at the time of impression taking, and the infectious diseases are caught to the dental professional via the impression material.

In order to solve these problems, for example, it is demanded to acquire information such as a three-dimensional shape in the oral cavity of a patient by using a non-contact type optical scanner as an intraoral digital impression taking device. It should be noted that herein, the "intraoral digital impression taking device" may be referred to as "impression taking device".

In addition, by manufacturing the prosthetic device by machining with the dental CAD/CAM system by using the three-dimensional image data obtained by the impression taking device, it is required to achieve improvement in productivity, uniformity of quality, and reduction in treatment period.

The dental CAD/CAM system includes, for example, a measuring device, a designing device, and/or a processing device, and manufactures the prosthetic device by machining. A dental CAD/CAM system using an impression taking device has been clinically applied in Europe and the United States since 1985.

However, the dental CAD/CAM system using the impression taking device is only used for prosthodontic treatment for one tooth such as inlay and/or crown from the viewpoint of three-dimensional measuring accuracy of impression taking device, and processing accuracy of processing device and from the reason that there are few dental materials that can be processed by a processing device.

The impression taking device is a device for three-dimensionally measuring the inside of an oral cavity while applying LED light or laser light, detecting the light reflected on the tooth surface with a scanner, and creating continuous three-dimensional image data by dedicated software.

The method of measuring the three-dimensional shape with the impression taking device adopts a confocal method, an active triangulation method, a light-interference tomography method, an active waveform sampling method, a moire tomography method, a combined use method of a stereoscopic mirror and line projection, a combined use method of stereo photography and structured light projection, or the like.

As the attribute of the impression taking device, the area that can be three-dimensionally measured is small in the human oral cavity, and the range that can be three-dimensionally measured with one shot is limited. For this reason, the impression taking device successively acquires a plurality of pieces of three-dimensional image data and connects the plurality of pieces of three-dimensional image data to create continuous three-dimensional image data. Specifically, the impression taking device connects a plurality of pieces of three-dimensional image data obtained by three-dimensional measuring by dedicated software. For example, the impression taking device detects portions having similar three-dimensional shapes in a plurality of pieces of three-dimensional image data by dedicated software. The impression taking device uses the detected similar portions as a reference for alignment and connects a plurality of pieces of three-dimensional image data to create three-dimensional image data. In this case, in the impression taking device, errors may occur in the detection of the portions having the similar three-dimensional shapes in the plurality of pieces of three-dimensional image data. Therefore, there is a problem that a plurality of pieces of three-dimensional image data cannot be accurately aligned and connected together.

In recent years, with the improvement in computer three-dimensional image processing ability and the optimization of three-dimensional measurement path, in clinical dentistry, it is possible to connect continuous three-dimensional images of the dental arch without destroying the data. However, it is difficult to improve the precision and accuracy of detection of portions having similar three-dimensional shapes in a plurality of pieces of three-dimensional image data obtained by three-dimensional measuring within a three-dimensional measurement range of one shot 25.00 mm$^2$ or more and 625.00 mm$^2$ or less. For this reason, even if the detected portions having similar three-dimensional shapes are used as a reference for alignment, it is difficult to precisely and accurately align and connect a plurality of pieces of three-dimensional image data. For example, it is difficult to accurately align and connect a plurality of pieces of three-dimensional image data obtained by three-dimensionally measuring an edentulous jaw, an isolated tooth abutment tooth, a bridge abutment tooth, a front tooth abutment tooth, a facial defect portion, and the like having similar three-dimensional shapes. For this reason, from the viewpoint of manufacturing precision of the prosthetic device, application cases of the impression taking device are currently limited to those having a small three-dimensional measurement range such as crown or inlay.

In the future, if it becomes possible to precisely and accurately acquire three-dimensional image data such as the oral area, the implant scan body, and the face, application cases of a dental CAD/CAM system being one component of an impression taking device are expected to spread. If application cases of a dental CAD/CAM system using an impression taking device spread, the transition from manual prosthetic device manufacturing to prosthetic device manufacturing using a dental CAD/CAM system will proceed. Thus, in prosthetic device manufacturing, it is possible to achieve work efficiency improvement and quality uniformization, to shorten the treatment period of patients with dental diseases, and to contribute to reducing the work burden of dental professionals.

In addition, with the advancement and digitization of dental medical technology, it is required to accurately aligning three-dimensional oral area tomographic data such as the running of nerve unique to the patient, thickness of alveolar bone, and temporomandibular joint obtained by computed tomography (CT)/magnetic resonance imaging (MRI), three-dimensional image data of the oral area model obtained by CT, a desktop scanner for the dental technique, and the patient's oral area three-dimensional image data obtained by an impression taking device and the like. In addition, it is required to easily correct the dimension of the three-dimensional oral area tomographic data into an accurate size. Furthermore, not only applying this to various treatment simulations in virtual reality, but also applying this to manufacturing actual prosthetic devices or surgical guides and the like by using data obtained by accurately aligning the three-dimensional oral area tomographic data and the oral area three-dimensional data is required.

Then, the inventors of the present invention have reached the following invention.

An auxiliary instrument according to one aspect of the present invention is an auxiliary instrument for dental use used as a reference of alignment for creating three-dimensional intraoral image data by connecting a plurality of pieces of three-dimensional image data obtained by three-dimensionally measuring an inside of an oral cavity, the auxiliary instrument including: a sheet portion having a first surface and a second surface opposed to the first surface; and a plurality of identification portions formed in a thickness direction of the sheet portion from the first surface of the sheet portion, each of the plurality of identification portions having a three-dimensional shape configured to be identified.

In the auxiliary instrument, the plurality of identification portions may have at least one shape of: a protrusion protruding in a direction opposite to a direction from the first surface toward the second surface of the sheet portion; a recess recessed from the first surface toward the second surface of the sheet portion; and a hole that allows communication between the first surface and the second surface of the sheet portion.

In the auxiliary instrument, shapes of adjacent identification portions of the plurality of identification portions may be different.

In the auxiliary instrument, the plurality of identification portions may have at least one shape of letters, numbers, signs, pictures, figures, emblems, patterns, symbols, and forms.

In the auxiliary instrument, each of the plurality of identification portions may be formed to have a dimension of 0.10 mm or more and 3.00 mm or less in a thickness direction of the sheet portion and formed to have a dimension of 0.10 mm or more and 20.00 mm or less in a longitudinal direction and a lateral direction when viewed in a thickness direction of the sheet portion.

In the auxiliary instrument, the auxiliary instrument may be formed of a material including a coloring agent recognized to have biological safety, the material to which an X-ray contrast medium is added.

In the auxiliary instrument, the sheet portion may have a rectangular shape having a thickness of 0.10 mm or more and 3.00 mm or less and a dimension of 1.00 mm or more and 200.00 mm or less in a longitudinal direction and a lateral direction when viewed in a thickness direction of the sheet portion.

In the auxiliary instrument, the sheet portion may have a semicircular shape when viewed in a thickness direction of the sheet portion, and an arcuate outer edge portion in the sheet portion may be bent from the first surface toward the second surface of the sheet portion.

In the auxiliary instrument, the sheet portion may be formed to be bent in a U shape when viewed in a thickness direction of the sheet portion, and may have a recessed cross-sectional shape recessed in a direction from the second surface toward the first surface of the sheet portion in a cross section of the sheet portion cut in a thickness direction.

The auxiliary instrument may include: a lip portion configured to widen and fix a lip of a patient; a mouth corner portion coupled to the lip portion by a coupling portion, the mouth corner portion configured to widen and fix a mouth corner of the patient; and a handle portion connected to the mouth corner portion, the handle portion configured to be gripped, and the sheet portion may be connected to the lip portion and/or the mouth corner portion and may extend from the lip portion and/or the mouth corner portion toward an inside of the oral cavity.

The auxiliary instrument may include: an upper jaw biteplate; and a lower jaw biteplate conforming to the upper jaw biteplate, the upper jaw biteplate may include: a first base plate portion including a first plate conforming to a form of an oral mucosa of an upper jaw of a patient, and the sheet portion extending from an end face of the first plate toward an oral mucosa of an upper jaw of the patient, the sheet portion provided with the plurality of identification portions; and a first bite rim portion disposed on an alveolus mucosa of the upper jaw, the first bite rim portion connected to the first plate of the first base plate portion, the plurality of identification portions may be formed on an end face of the first bite rim portion, the lower jaw biteplate may include: a second base plate portion including a second plate conforming to a form of an oral mucosa of a lower jaw of a patient, and the sheet portion extending from an end face of the second plate toward an oral mucosa of a lower jaw of the patient, the sheet portion provided with the plurality of identification portions; and a second bite rim portion disposed on an alveolus mucosa of the lower jaw, the second bite rim portion connected to the second plate of the second base plate portion, and the plurality of identification portions may be formed on an end face of the second bite rim portion.

A three-dimensional image data creation method of one aspect of the present invention is a three-dimensional image data creation method for creating three-dimensional intraoral image data by using an auxiliary instrument for dental use, the three-dimensional image data creation method including: while including an overlapping portion, three-dimensionally measuring an oral area in which an auxiliary instrument is disposed to acquire a plurality of pieces of three-dimensional image data obtained by three-dimensionally measuring both the auxiliary instrument and a shape in an oral cavity, the auxiliary instrument including a sheet portion having a first surface and a second surface opposed to the first surface, and a plurality of identification portions formed in a thickness direction of the sheet portion from the first surface of the sheet portion, each of the plurality of identification portions having a three-dimensional shape configured to be identified; identifying each shape of the plurality of identification portions of the auxiliary instrument in each of the plurality of pieces of three-dimensional image data; identifying one or a plurality of identification portions the shape of which is similar in the overlapping portion between the plurality of pieces of three-dimensional image data; aligning the plurality of pieces of three-dimensional image data by using the identified one or a plurality of identification portions as a reference of alignment; and connecting the aligned plurality of pieces of three-dimensional image data to create three-dimensional intraoral image data.

An aligning method of one aspect of the present invention is a method of aligning three-dimensional oral area tomographic data and three-dimensional intraoral image data using an auxiliary instrument for dental use, the method including: while including an overlapping portion, three-dimensionally measuring an oral area in which an auxiliary instrument is disposed to acquire a plurality of pieces of three-dimensional image data obtained by three-dimensionally measuring both the auxiliary instrument and a shape in an oral cavity, the auxiliary instrument including a sheet portion having a first surface and a second surface opposed to the first surface, and a plurality of identification portions formed in a thickness direction of the sheet portion from the first surface of the sheet portion, each of the plurality of identification portions having a three-dimensional shape configured to be identified; identifying each shape of the plurality of identification portions of the auxiliary instrument in each of the plurality of pieces of three-dimensional image data; identifying one or a plurality of identification portions the shape of which is similar in the overlapping portion between the plurality of pieces of three-dimensional image data; aligning the plurality of pieces of three-dimensional image data by using the identified one or a plurality of identification portions as a reference of alignment; connecting the aligned plurality of pieces of three-dimensional image data to create three-dimensional intraoral image data; CT scanning the oral area where the auxiliary instrument is disposed to acquire three-dimensional oral area tomographic data; in each piece of the three-dimensional intraoral image data and the three-dimensional oral area tomographic data, correcting dimensions of the three-dimensional intraoral image data and the three-dimensional oral area tomographic data so that the dimensions of the one or a plurality of identification portions are known dimensions; and aligning the corrected three-dimensional intraoral image data and three-dimensional oral area tomographic data based on the one or a plurality of identification portions.

Hereinafter, the present invention will be described with reference to the drawings. In all of the following drawings, the same or corresponding parts are denoted by the same reference numerals, and overlapping description will be omitted.

First Embodiment

[Auxiliary Instrument]

The auxiliary instrument is a dental auxiliary instrument used as a reference for creating three-dimensional intraoral image data by connecting a plurality of pieces of three-dimensional image data obtained by three-dimensional measuring in an oral cavity. The three-dimensional intraoral image data is image data representing a three-dimensional shape in the oral cavity of a patient.

FIG. 1 is a schematic diagram illustrating an example of the auxiliary instrument 10 according to a first embodiment of the present invention. The X, Y, and Z directions in FIG. 1 indicate the widthwise direction, lengthwise direction, and thickness direction of the auxiliary instrument 10, respectively. As illustrated in FIG. 1, the auxiliary instrument 10 includes a sheet portion 11 and a plurality of identification portions 12 provided in the sheet portion 11.

Hereinafter, the configuration of the auxiliary instrument 10 will be described in detail.

<Sheet Portion>

The sheet portion 11 is formed of a sheet-shaped member. Specifically, the sheet portion 11 is formed of a thin sheet-shaped member having a first surface and a second surface opposed to the first surface, and has a rectangular shape as viewed in the thickness direction, that is, in the Z direction. It should be noted that in the first embodiment, the first surface is described as the upper surface of the sheet portion 11 and the second surface is described as the lower surface of the sheet portion 11, but the present invention is not limited thereto. The first surface may be used as the lower surface of the sheet portion 11 and the second surface may be used as the upper surface of the sheet portion 11.

In addition, the sheet portion 11 is formed of an elastically deformable material. Therefore, the auxiliary instrument 10 can be deformed and disposed in the oral cavity according to the intraoral shape of the patient or the shape of the model.

In addition, the sheet portion 11 is formed of a material confirmed to have biological safety. Thus, it is possible to prevent adverse effect on the human body even when the sheet portion 11 is disposed in the oral cavity.

In addition, the sheet portion 11 is formed of a material to which an X-ray contrast medium is added. Thus, even in CT scan of the oral cavity, the auxiliary instrument 10 can be three-dimensionally measured. It should be noted that in the auxiliary instrument 10, the X-ray contrast medium is not indispensable.

The sheet portion 11 is formed in a sheet shape that can be disposed in the oral cavity of a patient or in the model. For example, the sheet portion 11 may have a shape such as a triangle, a rectangle, a rhombus, a circle, an ellipse, a semicircle, or the like.

In the first embodiment, as an example, the sheet portion 11 is formed in a substantially square shape when viewed in the thickness direction. The thickness of the sheet portion 11 is, for example, 0.1 mm or more and 3.0 mm or less. In addition, the dimensions of the sheet portion 11 in the longitudinal direction and the lateral direction when viewed in the thickness direction are 1.00 mm or more and 200.00 mm or less. Herein, the longitudinal direction means the X direction and the lateral direction means the Y direction.

It should be noted that the shape of the sheet portion 11 is not limited to a substantially square shape and may be a shape corresponding to the intraoral shape of the patient. FIG. 2 is a schematic view of an auxiliary instrument 10A of a modified example. As illustrated in FIG. 2, in the auxiliary instrument 10A, the outer edge portion 13 of the sheet portion 11a is formed to cover the gingival region of the patient. The gingival region is a part of the oral mucosa and surrounds the root of the tooth.

Specifically, the sheet portion 11a is formed in a semi-circular shape. The portion curved at the outer edge portion of the sheet portion 11a is bent in the thickness direction of the sheet portion 11. Specifically, the arc-shaped outer edge portion 13 in the sheet portion 11a is bent from the first surface (upper surface) toward the second surface (lower surface) of the sheet portion 11. In addition, the central portion 14 of the sheet portion 11a is recessed in a direction from the first surface toward the second surface.

Figure 3:
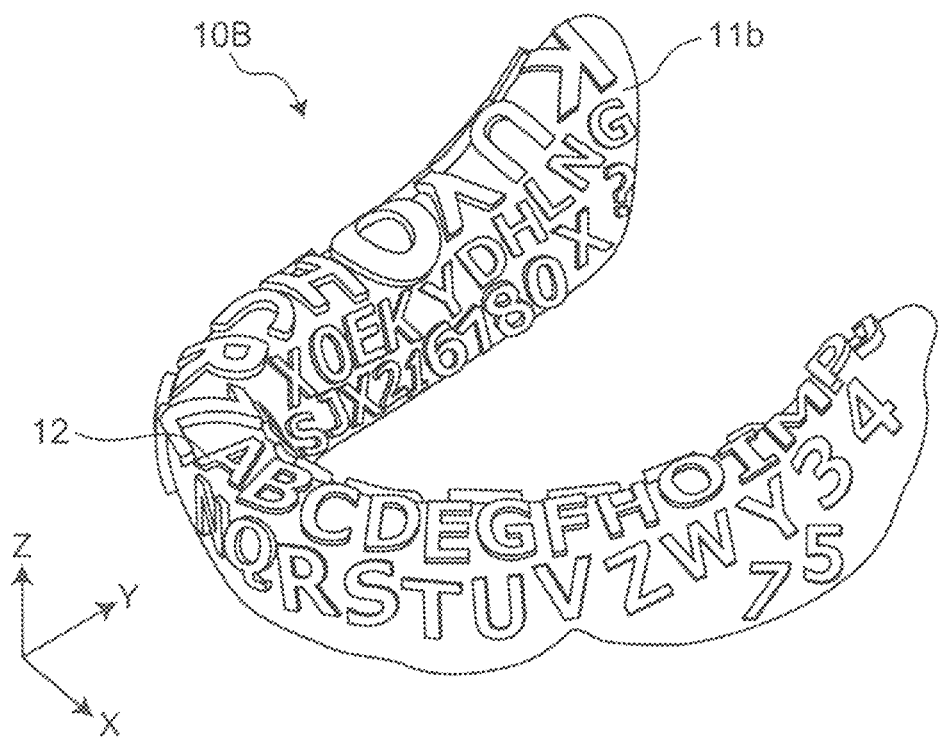
FIG. 3 is a schematic diagram illustrating an auxiliary instrument of another modified example according to the first embodiment of the present invention.

FIG. 3 is a schematic view of an auxiliary instrument 10B of another modified example. As illustrated in FIG. 3, in the auxiliary instrument 10B, the sheet portion 11b is formed to cover the gingiva of the patient. Specifically, the sheet portion 11b may be formed by being bent in a U shape when viewed in the thickness direction of the sheet portion 11b, and may have a recessed cross-sectional shape recessed in the thickness direction of the sheet portion 11b, that is, in a direction from the second surface toward the first surface in the cross section of the sheet portion 11b cut in the thickness direction.

Thus, forming the sheet portions 11a and 11b to cover the gingiva of the patient makes it easier to dispose the auxiliary instruments 10A and 10B in the oral cavity.

<A Plurality of Identification Portions>

Returning to FIG. 1, the plurality of identification portions 12 are formed in the thickness direction of the sheet portion 11, that is, in the Z direction from the first surface (upper surface) of the sheet portion 11, and have respective identifiable three-dimensional shapes.

The "respective identifiable three-dimensional shapes" mean that the respective plurality of three-dimensional shapes represented by a plurality of pieces of three-dimensional image data obtained by three-dimensional measuring with the impression taking device can be identified by a control device.

The control device is, for example, a computer that stores a plurality of pieces of three-dimensional image data obtained by three-dimensional measuring with an impression taking device and creates three-dimensional intraoral image data by connecting a plurality of pieces of three-dimensional image data. In addition, the control device controls the impression taking device. The control device may be included in the impression taking device or may be configured separately from the impression taking device. In the first embodiment, the control device is configured separately from the impression taking device.

The control device includes one or more processors and a memory.

The one or more processors are, for example, a central processing unit (CPU), a microprocessor, or other processing unit capable of executing computer executable instructions. The processor is capable of executing the instructions stored in the memory.

The memory stores data of the control device. The memory includes, for example, a computer recording medium, and includes memory technology such as a RAM, a ROM, an EEPROM, or a flash memory, an optical disk storage such as a CD-ROM or a DVD, a magnetic storage device such as a magnetic cassette, a magnetic tape, or a magnetic disk storage, or any medium that can be used to store desired information and can be accessed by the control device.

The memory stores a plurality of pieces of three-dimensional image data obtained by three-dimensional measuring with the impression taking device. In addition, the memory stores a program for executing a method of creating three-dimensional intraoral image data by connecting a plurality of pieces of three-dimensional image data obtained by three-dimensionally measuring the inside of the oral cavity based on the auxiliary instrument 10.

The plurality of identification portions 12 include at least one shape of a protrusion protruding in a direction opposite to the direction from the first surface (upper surface) toward the second surface (lower surface) of the sheet portion 11, a recess recessed from the first surface toward the second surface of the sheet portion 11, and a hole that allows communication between the first surface and the second surface of the sheet portion 11. Alternatively, the plurality of identification portions 12 may be a combination of at least two of the protrusion, the recess, and the hole.

In each of the auxiliary instruments 10, 10A, and 10B illustrated in FIGS. 1 to 3, each of the plurality of identification portions 12 is formed of a protrusion that protrudes in a direction opposite to the direction from the first surface toward the second surface of the sheet portion 11. The plurality of identification portions 12 are regularly arranged at intervals in the X direction and the Y direction of the sheet portion 11. In addition, it is preferable that the shapes of the adjacent identification portions of the plurality of identification portions 12 are different. With this configuration, the control device can easily identify each of the plurality of identification portions 12.

The plurality of identification portions 12 are formed of the same material as that of the sheet portion 11.

The plurality of identification portions 12 have different three-dimensional shapes within a three-dimensional measuring range of, for example, 25.00 $mm^2$ or more and 625.00 $mm^2$ or less in an area three-dimensionally measured with one shot by the impression taking device. Specifically, the plurality of identification portions 12 have contours that can be identified as respective different shapes by the control device. For example, the plurality of identification portions 12 include shapes such as letters, numbers, signs, pictures, figures, emblems, patterns, symbols, forms, and combinations thereof.

The figure means a variety of shapes determined by a fixed rule. The figure may be, for example, a rectangular parallelepiped.

Figure 4:
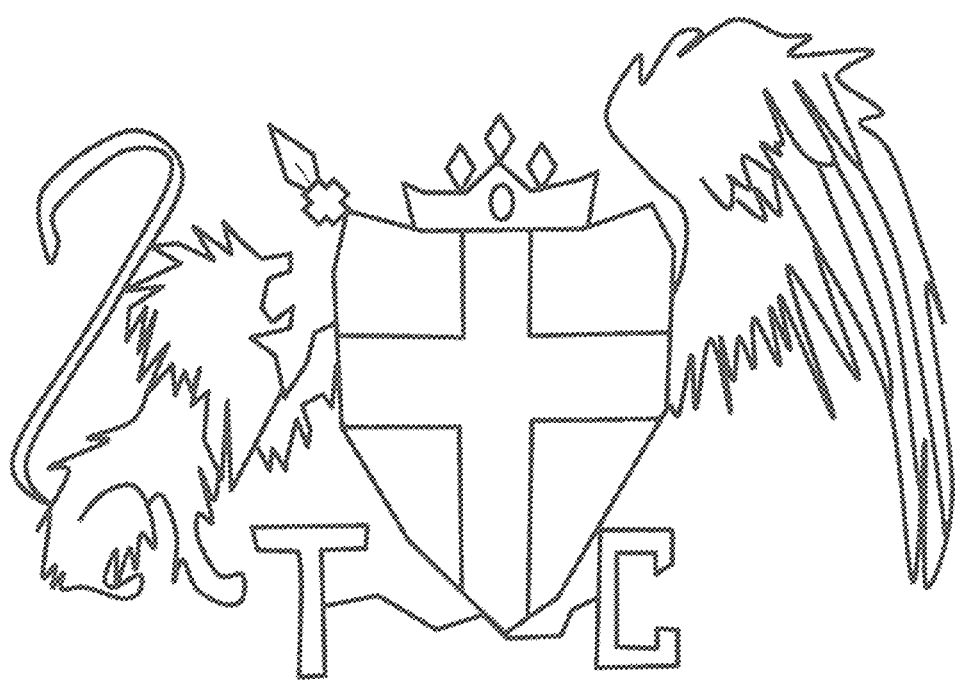
FIG. 4 is a diagram illustrating an example of an emblem.

FIG. 4 illustrates an example of an emblem. As illustrated in FIG. 4, the emblem means a design or a device that identifies and specifies an organization and a group such as a local government, a national government, a school, a public institution, a union (guild), and military forces as well as individuals and family lines.

Figure 5:
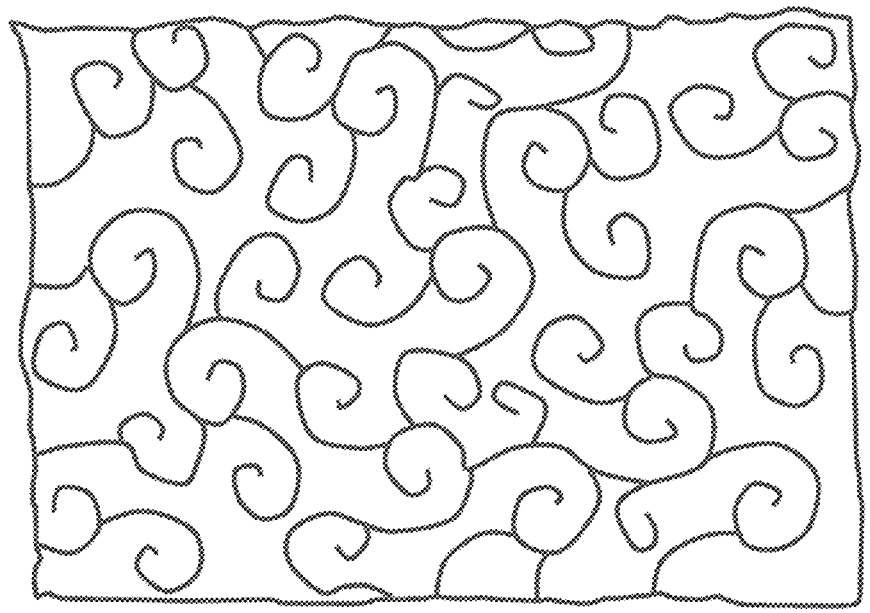
FIG. 5 is a diagram illustrating an example of a pattern.

FIG. 5 illustrates an example of a pattern. As illustrated in FIG. 5, the pattern means various pictures or shapes to be applied as decoration to fabrics, dye goods, crafts, and the like. In addition, the pattern may be a figure appearing on the surface of the object.

Figure 6:
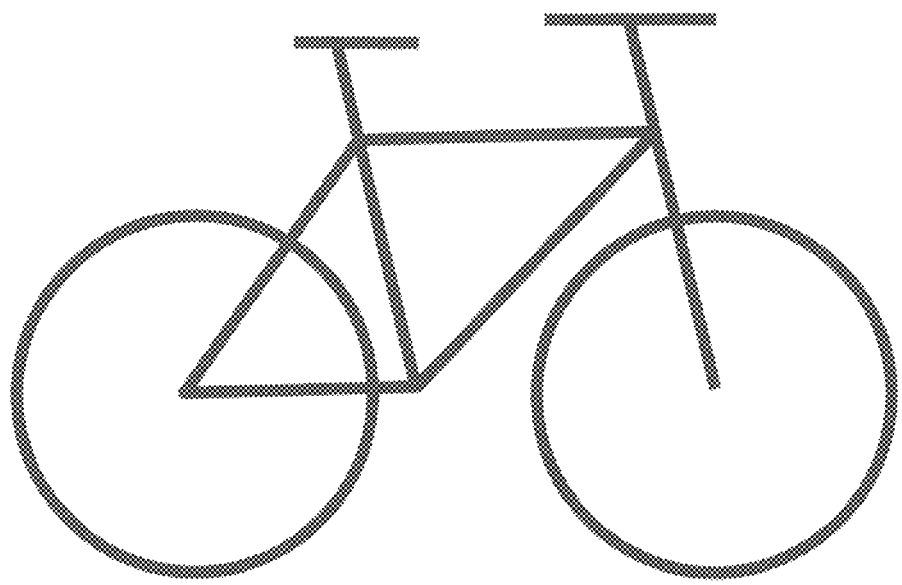
FIG. 6 is a diagram illustrating an example of a symbol.

FIG. 6 illustrates an example of a symbol. As illustrated in FIG. 6, the symbol is a sign having a certain meaning. In addition, the symbol may be a number, a letter, a figure representing a gesture, or the like having a certain meaning.

Figure 7:
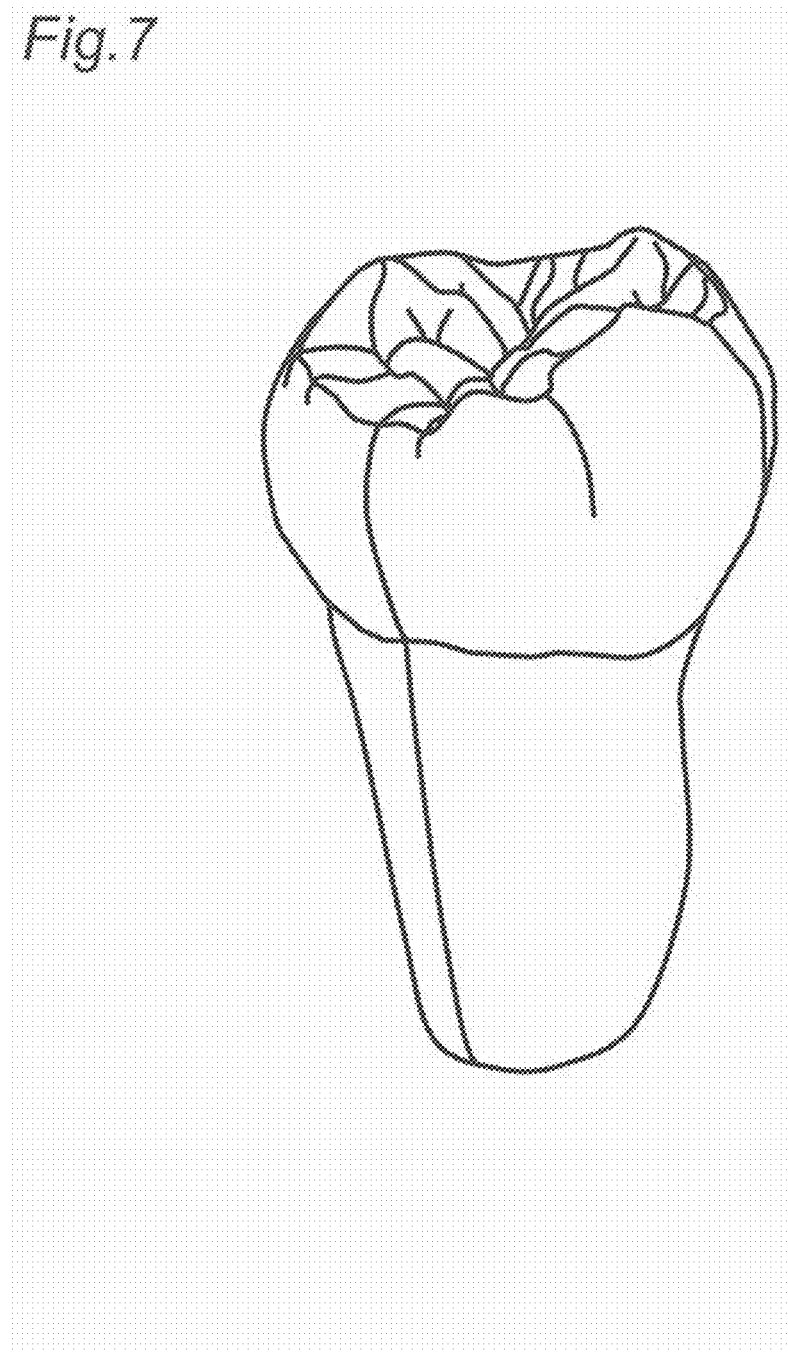
FIG. 7 is a diagram illustrating an example of a form.

FIG. 7 illustrates an example of a form. As illustrated in FIG. 7, the form is a shape or state of a tissue such as an object or mechanism viewed from the outside.

In the first embodiment, the plurality of identification portions 12 are formed of various alphabetic letters.

Each of the plurality of identification portions 12 is formed to have a dimension of 0.10 mm or more and 3.00 mm or less in the thickness direction of the sheet portion 11, and is formed to have a dimension of 0.10 mm or more and 20.00 mm or less in the longitudinal direction and the lateral direction as viewed in the thickness direction of the sheet portion 11.

In the first embodiment, the example in which the plurality of identification portions 12 are regularly arranged at intervals in the X direction and the Y direction of the sheet portion 11 is described, but the present invention is not limited thereto. For example, the plurality of identification portions 12 may be randomly arranged. In addition, the shapes of the adjacent identification portions of the plurality of identification portions 12 do not have to be different from each other.

[Manufacturing Method of Auxiliary Instrument]

Figure 8:
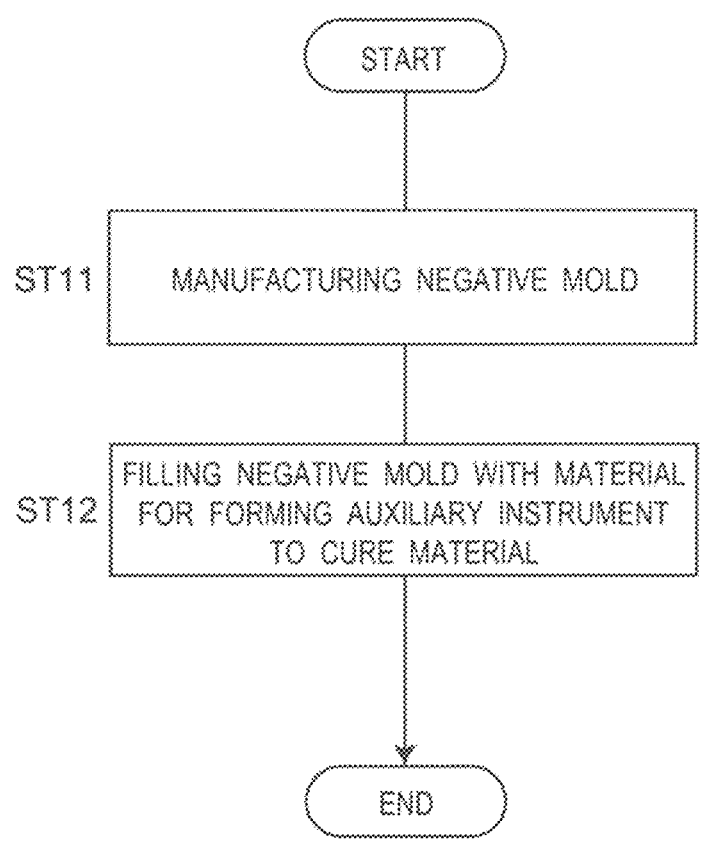
FIG. 8 is a flowchart of an example of a manufacturing method of the auxiliary instrument according to the first embodiment of the present invention.

An example of a manufacturing method of the auxiliary instrument 10 will be described with reference to FIG. 8. FIG. 8 is a flowchart of an example of a manufacturing method of the auxiliary instrument 10. As illustrated in FIG. 8, the manufacturing method of the auxiliary instrument 10 includes a step ST11 of manufacturing a negative mold and a step ST12 of filling and curing the material for forming the auxiliary instrument 10 in the manufactured negative mold.

In step ST11, a negative mold that forms the shape of the auxiliary instrument 10 is manufactured. The negative mold is a mold that forms the sheet portion 11 of the auxiliary instrument 10 and the plurality of identification portions 12.

For example, the negative mold includes a first recess formed in the shape of the sheet portion 11 of the auxiliary instrument 10. The first recess corresponding to the outer shape of the auxiliary instrument 10 means a portion to be filled with the material for forming the auxiliary instrument 10. On the bottom surface of the first recess, a plurality of recesses and protrusions for forming the plurality of identification portions 12 are formed. The plurality of recesses and protrusions have shapes corresponding to the shapes of the plurality of identification portions 12.

In the first embodiment, each of the plurality of identification portions 12 is formed as a protrusion protruding in a direction opposite to the direction from the first surface (upper surface) toward the second surface (lower surface) of the sheet portion 11. Therefore, on the bottom surface of the first recess, a plurality of second recesses corresponding to the shapes of the alphabetic letters axe formed. The plurality of second recesses are formed to be recessed in the direction from the first surface toward the second surface of the sheet portion 11 on the bottom surface of the first recess.

It should be noted that when the plurality of identification portions 12 are formed with recesses recessed from the first surface toward the second surface of the sheet portion 11 or holes for allowing communication between the first surface and the second surface of the sheet portion 11, a plurality of protrusions corresponding to the shapes of the alphabetic letters are formed on the bottom surface of the first recess. The plurality of protrusions are formed to be protruding in the direction from the second surface toward the first surface of the sheet portion 11 on the bottom surface of the first recess.

In the manufacturing of the negative mold, three-dimensional negative mold design data is created by a computer. For example, three-dimensional negative mold design data may be created by three-dimensional computer aided design (CAD). And, based on the three-dimensional negative mold design data, processing data may be created by computer aided manufacturing (CAM) software.

Next, based on the processing data, a negative mold is manufactured. For example, the negative mold is manufactured by a cutting machine or a 3D printer based on three-dimensional negative mold design data. Alternatively, the negative mold is manufactured by a laser processing machine, ultrasonic machining, or the like based on three-dimensional negative mold design data.

Three-dimensional CAD is one of the types of CAD that designs and drafts industrial products or buildings, and displays and edits a model three-dimensionally for drawing.

The CAM is a system for executing, for example, an NC program for processing, or the whole production preparation such as creation of slice data for processing with a 3D printer on the computer with shape data created with CAD to manufacture a product as input data.

The 3D printer means a device that adds a material of a three-dimensional model to a certain space. A highly accurate three-dimensional model is completed based on 3D data. Examples of the shaping system of 3D printing (3D printing system) include a material extrusion (heat melting layer), liquid phase photopolymerization (stereolithography), material injection (ink jet), binder injection, powder bed fusion bond, sheet layering, and directional energy deposition. Any shaping system may be selected depending on the material to be used.

The laser processing means performing engraving, cutting, drilling, or marking processing on various materials including, for example, metal, wood, leather, and the like with a laser beam.

The ultrasonic machining means a processing method of mixing the abrasive grains with a processing liquid such as water, interposing this between a tool that vibrates at high frequency and the workpiece, and performing an impact crushing action on the workpiece via the abrasive grain with the tool. The frequency of the tool is preferably 15.00 kHz or more and 50.00 kHz or less, and the amplitude is preferably 1.00 μm or more and 150.00 μm or less.

Surface treatment such as sandblast treatment, vaseline, or silicone separation material application may be applied to the surface of the manufactured negative mold.

Sandblast treatment is a treatment method in which an abrasive is mixed with compressed air and blown. The abrasive is, for example, alumina or glass beads. The pressure of the air compressor attached to the sand blaster is preferably 1.00 MPa or more.

The negative mold is made of a material that does not chemically react with the material for forming the auxiliary instrument 10.

In the first embodiment, in the negative mold, the first recess corresponding to the shape of the sheet portion 11 of the auxiliary instrument 10 is formed in a rectangular shape. One side of the first recess is, for example, 50.00 mm or more and 100.00 mm or less in width and 40.00 mm or more and 80.00 mm or less in length. In addition, the depth of the first recess is designed to be, for example, 0.10 mm or more and 3.00 mm or less. For example, the first recess may be formed by cutting a plate-shaped member with a cutting machine, or may be formed by providing a frame body on the plate-shaped member.

In addition, a plurality of second recesses formed corresponding to the shapes of the plurality of alphabetic letters corresponding to the plurality of identification portions 12 are provided on the bottom surface of the first recess. The depth of each of the plurality of second recesses is, for example, 0.10 mm or more and 3.00 mm or less. The length and width dimensions of each of the plurality of second recesses are, for example, 0.10 mm or more and 20.00 mm or less. The interval between the plurality of second recesses is 0.10 mm or more and 2.00 mm or less.

In step ST12, the negative mold manufactured in step ST11 is filled with the material for forming the auxiliary instrument 10 and the material is cured.

Examples of materials for forming the auxiliary instrument 10 include various compositions, polymer materials, thermoplastic resins, polymer gels, and the like. Examples of the various compositions include a dental resin composition, a dental silicone impression material composition, a dental alginate impression material composition, a dental agar impression material composition, and the like. Examples of the polymer material include a polymer material having elasticity or viscosity such as a resin for stereolithography, a rubber-like resin for stereolithography, a silicone resin for stereolithography, and the like. Examples of the thermoplastic resin include thermoplastic resins such as polypropylene, polyethylene, polyvinyl chloride, polystyrene, polyvinyl acetate, polyurethane, Teflon (registered trademark), ABS resin, AS resin, acrylic resin and the like. Examples of the polymer gel include polymer gels such as double network gel, nanocomposite gel, polyrotaxane and the like. In addition to these, examples of the material for forming the auxiliary instrument 10 include natural rubber latex, gutta-percha, and the like.

In addition, the material for forming the auxiliary instrument 10 is mixed with a coloring agent and an X-ray contrast medium recognized to have biological safety. As the coloring agent, for example, one having a color different from that in the oral cavity is used. The coloring agent only has to have a color capable of being three-dimensionally measured with an optical impression taking device, and specifically the coloring agent only has to have a color other than black. For example, the coloring agent may have blue, green, or the like.

In step ST12, the material for forming the auxiliary instrument 10 is poured into a negative mold and formed while being defoamed. For example, the base material of addition type silicone rubber used in clinical dentistry and the catalyst material are kneaded one to one. Next, air bubbles are removed with an air gun or the like while the kneaded silicone rubber is being injected into the negative mold. Thereafter, the material is cured by an addition reaction, the burrs are removed, and the formed object is taken out from the negative mold.

Thus, performing the steps ST11 and ST12 allows the auxiliary instrument 10 to be manufactured. It should be noted that the auxiliary instruments 10A and 10B of the modified examples illustrated in FIGS. 2 and 3 can also be manufactured by using the manufacturing method described above by changing the shape of the negative mold, that is, the shape of the first recess.

It should be noted that in step ST12, a thermoplastic resin may be used as a material for forming the auxiliary instrument 10. In this case, in step ST12, the auxiliary instrument 10 may be manufactured by injection molding using a thermoplastic resin.

Injection molding means applying injection pressure to a thermoplastic resin heated to a softening temperature to push the resin into a negative mold, fill the negative mold, and form the product.

Examples of the thermoplastic resin include polypropylene, polyethylene, polyvinyl chloride, polystyrene, polyvinyl acetate, polyurethane, Teflon (registered trademark), ABS resin, AS resin, acrylic resin, and the like. In addition, it is preferable that the thermoplastic resin is mixed with a coloring agent and an X-ray contrast medium recognized to have biological safety.

The injection pressure is preferably in the range of 10.00 kgf/cm$^2$ or more and 3000.00 kgf/cm$^2$ or less. The heating temperature of the thermoplastic resin is preferably higher than the melting point or glass transition temperature of the thermoplastic resin by the range of 50.00° C. or more and 150.00° C. or less.

It should be noted that the above-described manufacturing methods of the auxiliary instrument 10 are exemplary methods and the present invention is not limited thereto. The manufacturing method of the auxiliary instrument 10 only has to be a method capable of manufacturing the auxiliary instrument 10 including the sheet portion 11 and the plurality of identification portions 12 formed on the first surface (upper surface) of the sheet portion 11.

The auxiliary instrument 10 may be manufactured by an additive fabrication method or a cutting process. For example, three-dimensional design data of the auxiliary instrument 10 may be created and the auxiliary instrument 10 may be manufactured by a 3D printer based on the three-dimensional design data. Alternatively, the auxiliary instrument 10 may be manufactured by cutting with a cutting machine based on the three-dimensional design data.

Figure 9:
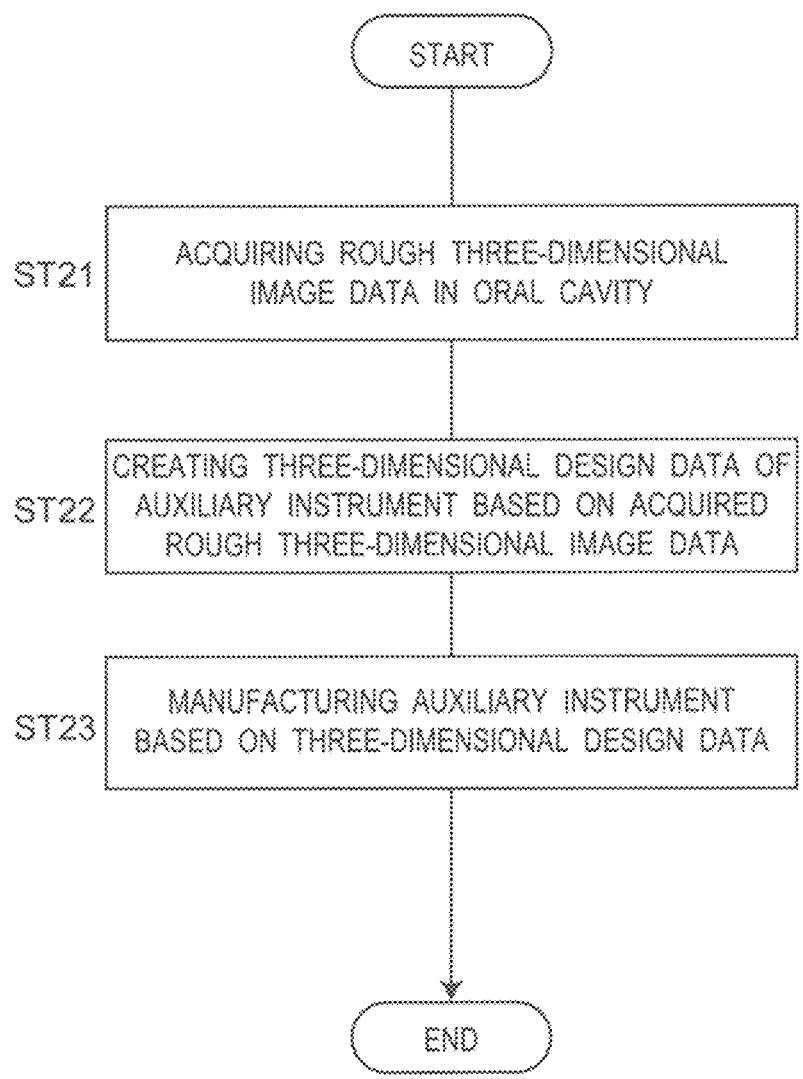
FIG. 9 is a flowchart of another example of a manufacturing method of the auxiliary instrument according to the first embodiment of the present invention.

Another example of the manufacturing method of the auxiliary instrument 10 will be described with reference to FIG. 9. FIG. 9 is a flowchart of another example of the manufacturing method of the auxiliary instrument 10. The manufacturing method illustrated in FIG. 9 is a method for manufacturing the auxiliary instrument 10 having a shape reflecting intraoral information of a patient.

As illustrated in FIG. 9, the method for manufacturing the auxiliary instrument 10 includes a step ST21 of acquiring rough three-dimensional image data in the oral cavity, a step ST22 of creating three-dimensional design data of the auxiliary instrument 10 based on the acquired rough three-dimensional image data, and a step ST23 of manufacturing the auxiliary instrument 10 based on the three-dimensional design data.

In step ST21, the digital rough impression taking is performed on the oral area of the patient or the model with the impression taking device. The digital rough impression taking means simple three-dimensional measurement of the three-dimensional shape in the oral cavity with a non-contact optical scanner or the like. Therefore, three-dimensional image data acquired by digital rough impression taking (hereinafter referred to as "rough three-dimensional image data") may have accuracy to the extent that the three-dimensional shape in the oral cavity can be grasped roughly, and may have low precision and accuracy in three-dimensional measurement. For example, it is preferable that the rough three-dimensional image data has an error from the measured value of the three-dimensional shape in the oral cavity of 0.00% or more and 30.00% or less.

The three-dimensional measurement method of the impression taking device can adopt, for example, a confocal method, an active triangulation method, a light-interference tomography method, an active waveform sampling method, a moire tomography method, a combined use method of a stereoscopic mirror and a line projection method, a combined use method of stereo photography and structured light projection method, or the like. Powder of titanium dioxide may be applied to the site to be three-dimensionally measured in order to prevent irregular reflection of teeth, prosthetic devices, and the like during three-dimensional measurement in the oral cavity.

In step ST21, the focus is set on the object to be three-dimensionally measured of the impression taking device and the impression taking device is caused to scan along the oral area being the site to be three-dimensionally measured. Thus, the shape in the oral cavity is continuously three-dimensionally measured and a plurality of pieces of three-dimensional image data are acquired. The impression taking device transmits a plurality of pieces of three-dimensional image data to the control device. The control device receives a plurality of pieces of three-dimensional image data and connects the plurality of pieces of three-dimensional image data by dedicated software. The connection of a plurality of pieces of three-dimensional image data are performed by using, for example, the shape of the gingiva or tooth row portion three-dimensionally measured (for example, curvature, edge, and the like) as a reference. Thus, rough three-dimensional image data that reproduces an approximate three-dimensional shape in the oral cavity peculiar to the patient is acquired.

In step ST21, three-dimensional image data of the face portion and the fingers of the limbs may be acquired in addition to the oral area of the patient by the impression taking device. The face portion means a front part of the head. Specifically, the face portion means a portion from the tip of the jaw to the hairline of the head in the vertical direction, and means a portion between the ears in the left-right direction.

In the first embodiment, an example in which the oral area is continuously three-dimensionally measured by the impression taking device in step ST21 is described, but the present invention is not limited thereto. For example, in step ST21, the oral area may be three-dimensionally measured a plurality of separate times without continuous three-dimensional measurement with the impression taking device.

In step ST22, three-dimensional design data of the auxiliary instrument 10 is created by using the rough three-dimensional image data in the oral cavity acquired in step ST21. Specifically, the control device creates three-dimensional design data of the auxiliary instrument 10 based on the rough three-dimensional image data in the oral cavity by using the program having the 3D modeling function stored in the memory. The control device executes a program stored in the memory, for example, based on the input from the user, and creates three-dimensional design data of the auxiliary instrument 10.

Based on the acquired rough three-dimensional image data in the oral cavity, the control device designs the auxiliary instrument 10 on the three-dimensional shape in the oral cavity reproduced by the program. Thus, the shape of the auxiliary instrument 10 that conforms to the rough three-dimensional shape in the oral cavity is modeled. That is, the control device creates data that reproduces the shape of the auxiliary instrument 10 on the rough three-dimensional image data.

For example, the control device performs determination of the attachment and detachment direction, removal of the undercut portion with respect to the attachment and detachment direction (hereinafter referred to as "blocking out"), setting of the outline of the sheet portion 11, setting of the thickness of the sheet portion 11, setting of the shape, size, number, and position of a plurality of identification portions 12, and the like. Thus, the control device sets the shape of the auxiliary instrument 10.

The attachment and detachment direction of the auxiliary instrument 10 is preferably perpendicular to the occlusal plane (a virtual plane connecting the three points of left and right lower jaw second molar distobuccal cusp tops and the midpoint of the mesial angle of the lower jaw central incisor). It is preferable to remove the undercut with respect to the attachment and detachment direction by blocking out the undercut portion based on the attachment and detachment direction of the auxiliary instrument 10 on the data.

In addition, the auxiliary instrument 10 is preferably designed so that the outer edge portion of the sheet portion 11 of the auxiliary instrument 10 is positioned downward in the range of 0.10 mm or more and 1.00 mm or less from the gingival margin of the abutment tooth in the rough three-dimensional image data in the oral cavity.

The outline of the auxiliary instrument 10 preferably does not exceed the gingival buccal mucosa transition portion and the palate portion of the maxilla. The thickness of the auxiliary instrument 10 is preferably 0.10 mm or more and 3.00 mm or less.

The shapes of the plurality of identification portions 12 are preferably different from each other. The size of each of the plurality of identification portions 12 is preferably 0.10 mm or more and 20.00 mm or less in length and width. When the plurality of identification portions 12 are formed of protrusions, the height of each of the plurality of identification portions 12 is preferably 0.10 mm or more and 3.00 mm or less. When the plurality of identification portions 12 are formed of recesses or holes, the depth of each of the plurality of identification portions 12 is preferably 0.10 mm or more and 3.00 mm or less. The interval between the plurality of identification portions 12 is preferably 0.10 mm or more and 20.00 mm or less.

Thus, the control device models the shape of the set auxiliary instrument 10 on the three-dimensional image data in the oral cavity to be reproduced by the rough three-dimensional image data in the oral cavity.

Next, the control device acquires the three-dimensional design data of the auxiliary instrument 10 by removing the rough three-dimensional image data in the oral cavity with the difference in Boolean operation from the data obtained by modeling the auxiliary instrument 10.

In step ST23, the auxiliary instrument 10 is manufactured based on the three-dimensional design data designed in step ST22. Specifically, the auxiliary instrument 10 is manufactured by the manufacturing device based on the three-dimensional design data of the auxiliary instrument 10. The manufacturing device means a device for manufacturing the auxiliary instrument 10, and is, for example, a 3D printer, a cutting machine, or the like. The manufacturing device is controlled by the control device. In the first embodiment, an example in which the manufacturing device is a 3D printer will be described.

For example, the control device creates output data with the CAM software for 3D printers based on the three-dimensional design data of the auxiliary instrument 10. The output data is data that can be read by the 3D printer. Examples of the output data include slice data and the like. The control device transmits the output data to the 3D printer.

The 3D printer receives the output data from the control device and manufactures the auxiliary instrument 10 based on the output data.

In the case of a 3D printer in a vat photopolymerization system, examples of the material to be used include, for example, a stereolithography resin, a stereolithography rubber-like resin, and a stereolithography silicone resin. In the case of a 3D printer in a FDM system, examples of the material to be used include a thermoplastic resin such as polypropylene, polyethylene, polyvinyl chloride, polystyrene, polyvinyl acetate, polyurethane, Teflon (registered trademark), an ABS resin, an AS resin, or an acrylic resin, or a polymer gel such as a double network gel, a nanocomposite gel, or polyrotaxane.

As described above, executing steps ST21 to ST23 allows the auxiliary instrument 10 having a shape reflecting intraoral information on the patient to be manufactured.

[Three-Dimensional Image Data Creation Method Using Auxiliary Instrument]

Figure 10:
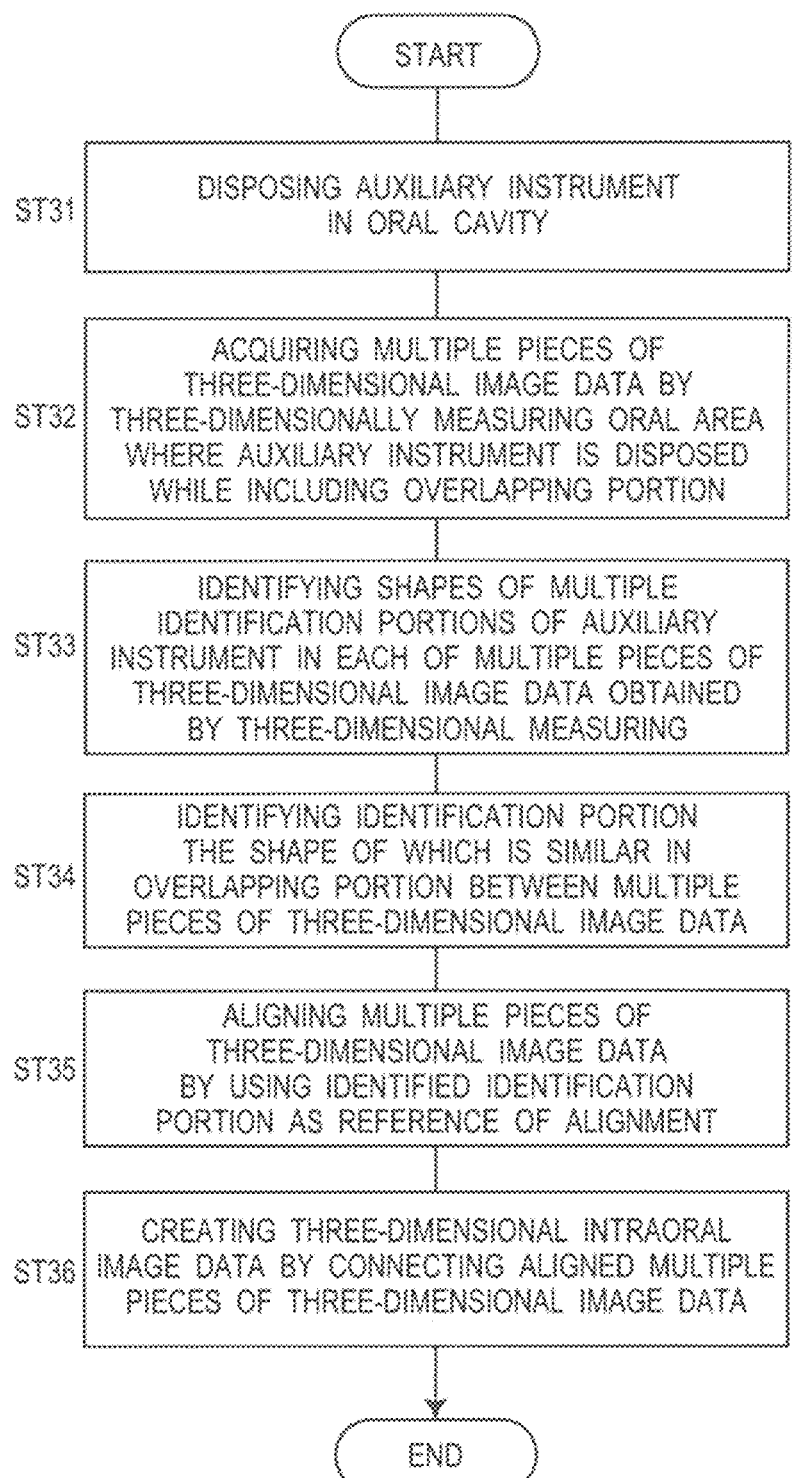
FIG. 10 is a flowchart of an example of a three-dimensional image data creation method using the auxiliary instrument according to the first embodiment of the present invention.

A three-dimensional image data creation method using the auxiliary instrument 10 will be described with reference to FIG. 10. FIG. 10 is a flowchart of an example of a three-dimensional image data creation method using the auxiliary instrument 10.

As illustrated in FIG. 10, in step ST31, the auxiliary instrument 10 is disposed in the oral cavity. The auxiliary instrument 10 is disposed in an oral area to be three-dimensionally measured by the impression taking device. Specifically, the auxiliary instrument 10 is disposed in the oral cavity of the patient or a model for reproducing the inside of the patient's oral cavity.

The auxiliary instrument 10 can be processed according to the portion desired to be three-dimensionally measured in the oral cavity. For example, when a portion to which a prosthetic device is to be attached is desired to be three-dimensionally measured in the oral cavity of the patient, a hole may be formed in the auxiliary instrument 10 so that the portion to which the prosthetic device is to be attached is exposed. Alternatively, when a dentition is desired to be three-dimensionally measured, the auxiliary instrument 10 may be cut so that the dentition portion is exposed.

Figure 11A:
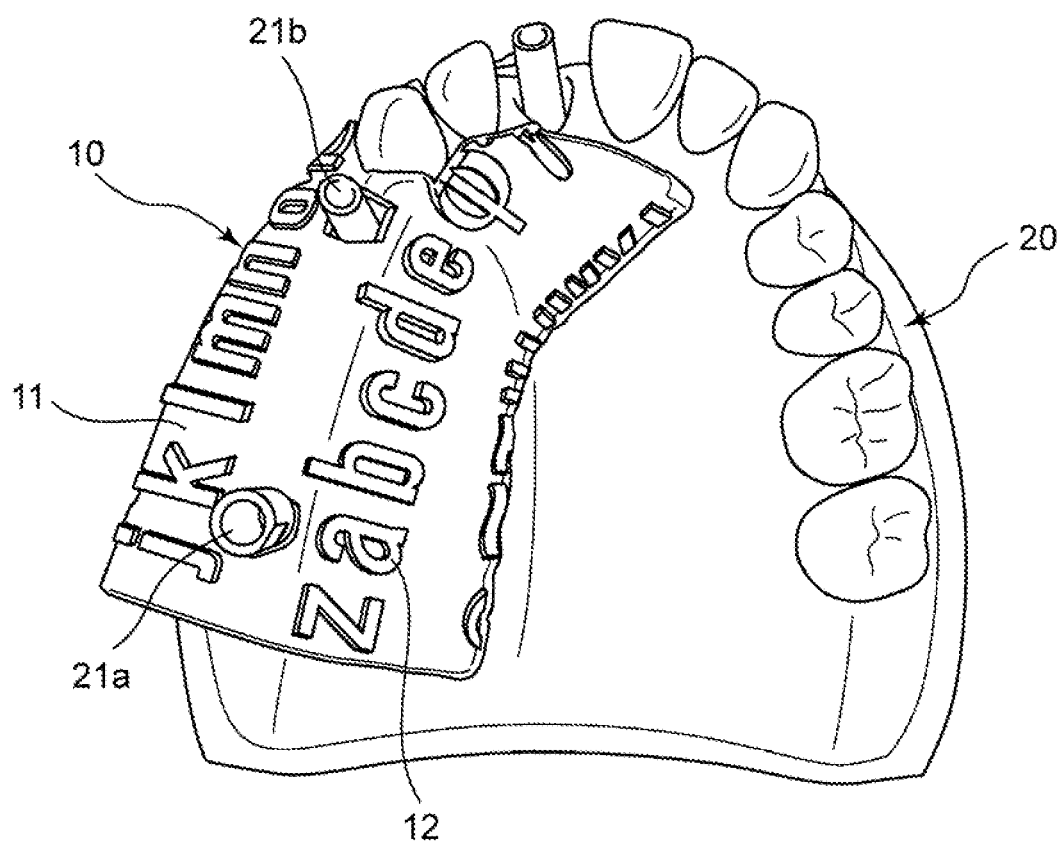
FIG. 11A is a diagram illustrating a part of an exemplary process of a three-dimensional image creation method.

FIG. 11A illustrates a part of an exemplary process of the three-dimensional image data creation method, and illustrates a state where the auxiliary instrument 10 is disposed in the oral cavity of the model 20. As illustrated in FIG. 11A, the auxiliary instrument 10 is provided with a hole at a position corresponding to the portions of the attachment pins 21a and 21b to which the prosthetic device is attached in the oral cavity, and is processed so that the attachment pins 21a and 21b are exposed.

Thus, in step ST31, the auxiliary instrument 10 is disposed in a portion desired to be three-dimensionally measured in the oral cavity, that is, a portion where three-dimensional image data is desired to be acquired in the oral cavity.

Returning to FIG. 10, in step ST32, three-dimensionally measuring an oral area where the auxiliary instrument 10 is disposed while including overlapping portions allows a plurality of pieces of three-dimensional image data to be acquired.

Figure 11B:
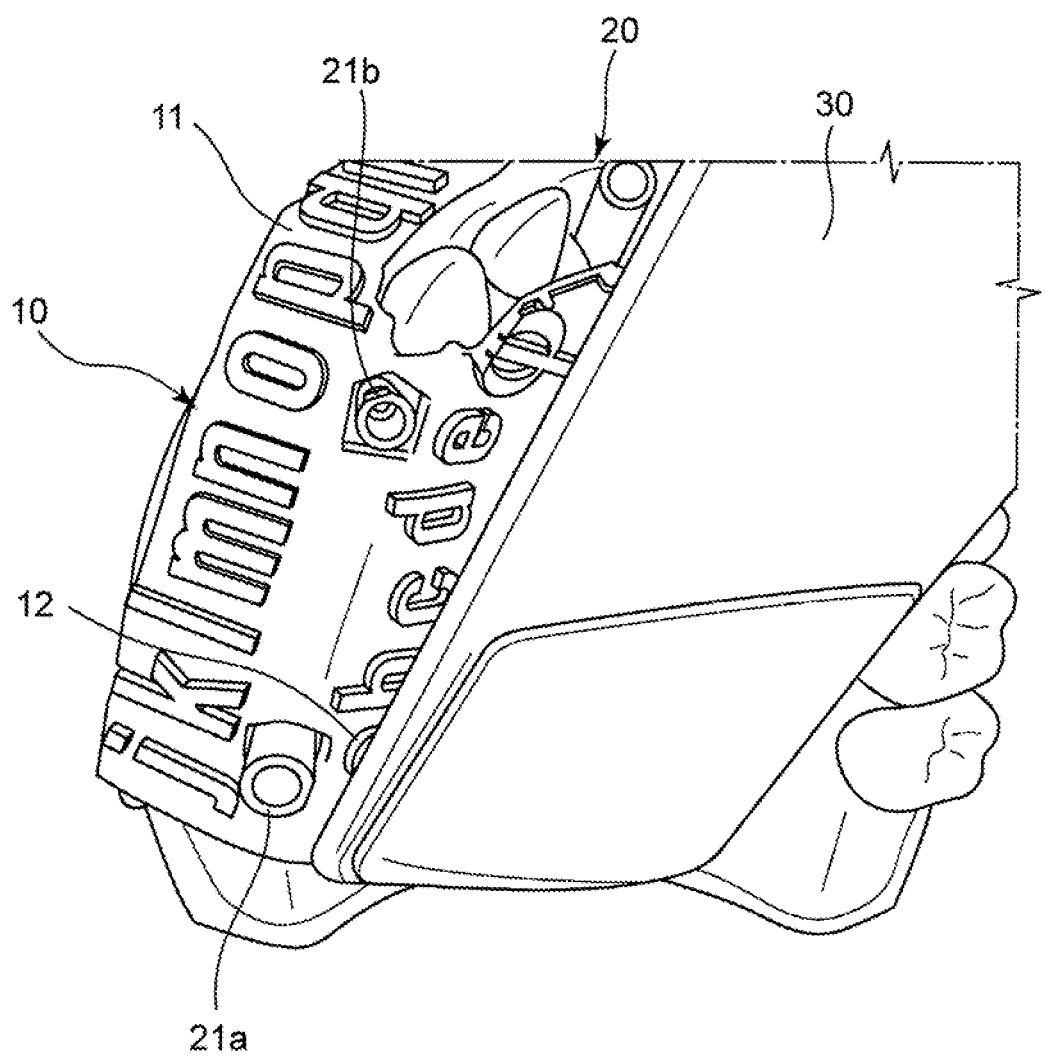
FIG. 11B is a diagram illustrating a part of an exemplary process of a three-dimensional image creation method.

FIG. 11B illustrates a part of an exemplary process of the three-dimensional image data creation method, and illustrates a state in which the oral area of the model 20 in which the auxiliary instrument 10 is disposed is three-dimensionally measured by the impression taking device 30. As illustrated in FIG. 11B, while the impression taking device 30 is moved in the oral cavity, the oral area where the auxiliary instrument 10 is disposed is three-dimensionally measured at a plurality of portions continuously. Thus, a plurality of pieces of three-dimensional image data are acquired obtained by three-dimensionally measuring the auxiliary instrument 10 together with the shape in the oral cavity.

The impression taking device 30 continuously three-dimensionally measures the oral area at a plurality of portions including the overlapping portion. Therefore, a plurality of pieces of three-dimensional image data obtained by continuous three-dimensional measuring, that is, two pieces of three-dimensional image data obtained by three-dimensional measuring before and after include overlapping portions.

The impression taking device 30 transmits the acquired plurality of pieces of three-dimensional image data to the control device.

Returning to FIG. 10, in step ST33, in each of the plurality of pieces of three-dimensional image data obtained by three-dimensional measuring, a corresponding one of the shapes of the plurality of identification portions 12 of the auxiliary instrument 10 is identified.

Specifically, the control device receives a plurality of pieces of three-dimensional image data from the impression taking device. Next, in each of the plurality of pieces of three-dimensional image data, the control device detects characteristics (for example, recesses and protrusions, outlines, and the like) of the respective plurality of identification portions 12. Thus, each of the three-dimensional shapes of the plurality of identification portions 12 appearing in the plurality of pieces of three-dimensional image data is identified.

In step ST34, one or a plurality of identification portions 12 the shape of which is similar in an overlapping portion between the plurality of pieces of three-dimensional image data are identified.

From the plurality of identification portions 12 having the three-dimensional shapes identified in step ST33, the control device identifies one or a plurality of identification portions 12 the three-dimensional shape of which is similar in the overlapping portion between the plurality of pieces of three-dimensional image data obtained by continuous three-dimensional measuring.

Specifically, the control device compares each of the three-dimensional shapes of the identified plurality of identification portions 12 in the overlapping portion between two consecutive pieces of three-dimensional image data. Thus, one or a plurality of identification portions 12 the shape of which is similar in the overlapping portion between two consecutive pieces of three-dimensional image data are identified. That the shape is similar means that the three-dimensional shapes of the identification portions 12 match with an error of, for example, 30.00 µm or less, preferably 10.00 µm or less.

In step ST35, one or a plurality of identification portions 12 identified in step ST34 are used as a reference of alignment, and a plurality of pieces of three-dimensional image data are aligned.

Specifically, the control device aligns the plurality of pieces of three-dimensional image data so that the three-dimensional shapes of one or a plurality of identification portions 12 the shape of which is similar in an overlapping portion of between the plurality of pieces of three-dimensional image data are superimposed. For example, the control device adjusts the position, angle, size, and the like of the three-dimensional shapes of one or a plurality of identification portions 12 in the overlapping portion of the plurality of pieces of three-dimensional image data so that the outlines of the three-dimensional shape of one or a plurality of similar identification portions 12 match with each other. Thus, it is possible to align a plurality of pieces of three-dimensional image data.

In step ST36, a plurality of aligned pieces of three-dimensional image data are connected. Specifically, the control device connects a plurality of pieces of three-dimensional image data aligned in step ST35.

Thus, executing steps ST31 to ST36 allows three-dimensional intraoral image data to be created.

It should be noted that the algorithms used for aligning a plurality of three-dimensional images are as follows. The processes A1 to A4 shown below are performed in steps ST33 and ST34 illustrated in FIG. 10. In addition, processes A1 to A4 are performed by the control device.

(Process A1)

Of characteristics such as voxels themselves or point sets of three-dimensional image data, which characteristic to be used is set (Setting of characteristic space). Specifically, characteristics of the identification portions represented by information such as voxels or point sets (for example, recesses and protrusions, outlines, and the like) are set as the characteristic space.

(Process A2)

In each piece of three-dimensional image data, a range for searching the characteristic space set in process A1 is set (Setting of search space).

(Process A3)

In each piece of three-dimensional image data, the characteristic space set in process A1 is detected within the search range set in process A2.

(Process A4)

The characteristic (shape) of each piece of three-dimensional image data obtained in up to Process A3 is expressed as a correlation function and the maximum value of the correlation function is calculated (Similarity measure). It should be noted that the correlation function is a function used for evaluation at the time of aligning a plurality of pieces of three-dimensional image data.

Alignment of a plurality of pieces of three-dimensional image data uses, for example, a cross-correlation method to calculate a correlation function between three-dimensional images as a similarity measure. For example, when first three-dimensional image data is expressed as a function A and second three-dimensional image data is expressed as a function B, the correlation function between the function A and the function B is calculated and the maximum value of the correlation function is obtained. The obtained maximum value indicates that the positional relationship between the two pieces of three-dimensional image data matches most. Thus, it is possible to detect the direction with the highest similarity among a plurality of pieces of three-dimensional image data and align a plurality of pieces of three-dimensional image data.

In the first embodiment, as an example, in process A1, a characteristic of identification portions is set as a characteristic space by using a point set. In process A2, when a rotation angle method is used, range designation and step size designation are set. Regarding translation, full search is set at pixel interval. In process A3, the characteristic space is detected while Euler angles are used and the three-dimensional image data is rotated. In process A4, the characteristic of each piece of three-dimensional image data is expressed as a correlation function, and the maximum value of the correlation function is calculated. Examples of the correlation function include a normal correlation function, a phase correlation function, and a method of taking phase correlation with the square root of intensity as a weight.

In the first embodiment, each time two consecutive pieces of three-dimensional image data are acquired, the two pieces of three-dimensional image data are aligned.

[Method of Aligning Three-Dimensional Oral Area Tomographic Data and Three-Dimensional Intraoral Image Data]

The method of aligning three-dimensional oral area tomographic data and three-dimensional intraoral image data using the auxiliary instrument 10 will be described with reference to FIG. 12. FIG. 12 is a flowchart of an example of a method of aligning three-dimensional oral area tomographic data and three-dimensional intraoral image data using the auxiliary instrument 10 according to the first embodiment of the present invention.

As illustrated in FIG. 12, in step ST41, three-dimensional intraoral image data is created. Specifically, step ST41 executes steps ST31 to ST36 illustrated in FIG. 10. The three-dimensional intraoral image data is three-dimensional intraoral image data obtained by three-dimensional measuring together with the auxiliary instrument 10.

Alternatively, the three-dimensional intraoral image data may be obtained by manufacturing a dentition model by a conventional impression method. In step ST41, the three-dimensional intraoral image data may be acquired by disposing the auxiliary instrument 10 in the dentition model and performing three-dimensional measurement with a desktop scanner for the dental technique.

In step ST42, three-dimensional oral area tomographic data is acquired by CT scan of the oral area where the auxiliary instrument 10 is disposed. Thus, three-dimensional oral area tomographic data is acquired together with the auxiliary instrument 10. The CT scan is performed, for example, by a CT imaging device. It should be noted that the CT imaging device is controlled by, for example, a control device.

The CT imaging device transmits three-dimensional oral area tomographic data to the control device.

In step ST43, the dimensions of the three-dimensional oral area tomographic data and the three-dimensional intraoral image data are corrected by using the plurality of identification portions 12 having known dimensions. Specifically, the dimensions of the three-dimensional oral area tomographic data and the three-dimensional intraoral image data are scaled to be corrected so that the dimensions of the plurality of identification portions 12 of the three-dimensional oral area tomographic data and the three-dimensional intraoral image data have known dimensions. The known dimension means a predetermined dimension and means an actual dimension of the identification portion 12.

In step ST44, based on the plurality of identification portions 12, the corrected three-dimensional oral area tomographic data and the three-dimensional intraoral image data are aligned. For example, the corrected three-dimensional oral area tomographic data and the three-dimensional intraoral image data are aligned by, for example, the iterative closest point method (ICP method), the reference point best fit method, the three-point alignment method, or the like.

Thus, the known dimensions of the identification portion 12 can be used for the dimension correction of the obtained three-dimensional oral area tomographic data and the three-dimensional intraoral image data. In addition, performing the dimension correction allows three-dimensional image alignment to be performed with higher accuracy than the conventional alignment.

It should be noted that in the method of determining the dimension of three-dimensional intraoral image data by using intraoral three-dimensional image data and three-dimensional oral area tomographic data, the auxiliary instrument 10 preferably uses an object formed of a material to which an X-ray contrast medium is added.

[Manufacturing Method of Prosthetic Device]

In addition, the three-dimensional image data creation method using the above-described auxiliary instrument 10 can also be used for a method for manufacturing a prosthetic device.

A method for manufacturing a prosthetic device includes, for example, a step of manufacturing a prosthetic device based on the created three-dimensional intraoral image data in addition to the steps ST31 to ST36 illustrated in FIG. 10.

In the step of manufacturing a prosthetic device, a prosthetic device conforming to the three-dimensional shape in the oral cavity is manufactured from the three-dimensional intraoral image data.

Specifically, the step of manufacturing a prosthetic device includes the following processes A11 to A16 in addition to the steps ST31 to ST36 illustrated in FIG. 10.

(Process A11)

The created three-dimensional intraoral image data is imported into the dental 3D CAD.

(Process A12)

The shape of each prosthetic device is designed based on the prosthetic dental design guidelines by using the dental 3D CAD.

(Process A13)

The 3D data of each designed prosthetic device is exported as STL format data.

(Process A14)

The created STL format data imported into the dental CAM software and data for cutting (NC data) or data for 3D printing (slice data) is created according to the machine tool used for processing.

(Process A15)

Cutting or 3D printing is performed by using the created output data (data for cutting or data for 3D printing).

For example, the machining material of the cutting process is zirconia, PMMA, wax, composite resin, glass fiber reinforced resin, cobalt chromium alloy, titanium alloy, pure titanium, or the like.

For example, the material for 3D printing is a resin for stereolithography, resin for FDM method, PEEK, ABS, zirconia, cobalt chromium alloy powder, titanium alloy powder, pure titanium powder, or the like.

(Process A16)

After the processing is completed, the rest and support are removed, and adjustment and polishing are performed. Thus, the prosthetic device is completed.

It should be noted that the prosthetic device includes various types such as an inlay, a crown, a bridge, and the like, the methods for manufacturing the prosthetic devices include the above processes, and the prosthetic devices can be manufactured. The difference is a detailed modeling method in the dental 3D CAD.

Effect

According to the auxiliary instrument, the manufacturing method of the auxiliary instrument, and the three-dimensional image data creating method using the auxiliary instrument according to the present invention, the following effects can be produced.

The auxiliary instrument 10 includes a sheet portion 11 having a first surface and a second surface opposed to the first surface, and a plurality of identification portions 12 formed in a thickness direction of the sheet portion 11 from the first surface (upper surface) of the sheet portion 11, each of the plurality of identification portions having a three-dimensional shape configured to be identified. With this configuration, when three-dimensional intraoral image data is created by connecting a plurality of pieces of three-dimensional image data obtained by three-dimensionally measuring the inside of the oral cavity, the plurality of identification portions 12 can be used as a reference of alignment of the plurality of pieces of three-dimensional image data. Thus, it is possible to improve precision and accuracy of three-dimensional intraoral image data.

The plurality of identification portions 12 have at least one shape of: a protrusion protruding in a direction opposite to a direction from the first surface toward the second surface of the sheet portion 11; a recess recessed from the first surface toward the second surface of the sheet portion 11; and a hole that allows communication between the first surface and the second surface of the sheet portion 11. With this configuration, since the plurality of identification portions 12 are easily identified by the control device, a plurality of pieces of three-dimensional image data can be easily aligned and connected together. Thus, it is possible to further improve precision and accuracy of three-dimensional intraoral image data.

The shapes of the adjacent identification portions of the plurality of identification portions 12 are different. With this configuration, since the plurality of identification portions 12 are more easily identified by the control device, the precision and accuracy of three-dimensional intraoral image data can be further improved.

The plurality of identification portions 12 have at least one shape of letters, numbers, signs, pictures, figures, emblems, patterns, symbols, and forms. With this configuration, since the plurality of identification portions 12 are more easily identified by the control device, the precision and accuracy of three-dimensional intraoral image data can be further improved.

Each of the plurality of identification portions 12 is formed to have a dimension of 0.10 mm or more and 3.00 mm or less in the thickness direction of the sheet portion 11, and is formed to have a dimension of 0.10 mm or more and 20.00 mm or less in the longitudinal direction and the lateral direction as viewed in the thickness direction of the sheet portion 11. With this configuration, since the plurality of identification portions 12 are more easily identified by the control device, the precision and accuracy of three-dimensional intraoral image data can be further improved.

The auxiliary instrument 10 is formed of a material including a coloring agent recognized to have biological safety. With this configuration, coloring the color of the auxiliary instrument 10 to be different from the color in the oral cavity allows the identification portions 12 to be made more easily identified. Thus, it is possible to further improve precision and accuracy of three-dimensional intraoral image data.

The auxiliary instrument 10 is formed of a material to which an X-ray contrast medium is added. With this configuration, it is possible to three-dimensionally measure the shape of the auxiliary instrument 10 even in CT scanning.

The sheet portion 11 has a rectangular shape having a thickness of 0.10 mm or more and 3.00 mm or less and a dimension of 1.00 mm or more and 200.00 mm or less in a longitudinal direction and a lateral direction when viewed in a thickness direction of the sheet portion 11. With this configuration, there is an advantage that it is easy to dispose the auxiliary instrument 10 in the oral cavity or around the face portion.

In the auxiliary instrument 10A, the sheet portion 11a has a semicircular shape when viewed in a thickness direction (Z direction) of the sheet portion 11a, and an arcuate outer edge portion in the sheet portion 11a is bent from the first surface toward the second surface of the sheet portion 11a. With this configuration, the shape of the auxiliary instrument 10A can have a shape corresponding to the gingiva shape of the patient, and the auxiliary instrument 10 can be easily disposed in the oral cavity.

In the auxiliary instrument 10B, the sheet portion 11b is formed to be bent in a U shape when viewed in a thickness direction of the sheet portion 11b, and has a recessed cross-sectional shape recessed in a direction from the second surface toward the first surface of the sheet portion 11b in a cross section of the sheet portion 11b cut in a thickness direction. With this configuration, the shape of the auxiliary instrument 10B can be a shape more corresponding to the gingiva shape of the patient, and the auxiliary instrument 10B can be disposed more easily in the oral cavity.

Example

As Example 1, an example of three-dimensional intraoral image data acquired by executing a creation method of three-dimensional image data using the auxiliary instrument 10 according to the first embodiment of the present invention will be described. In addition, as Comparative Example 1, an example of creating three-dimensional image data without using the auxiliary instrument 10 will also be described. It should be noted that in both Example 1 and Comparative Example 1, three-dimensional intraoral image data was created by continuously three-dimensionally measuring the inside of the oral cavity of the model with an impression taking device and connecting a plurality of pieces of three-dimensional image data.

Figure 13:
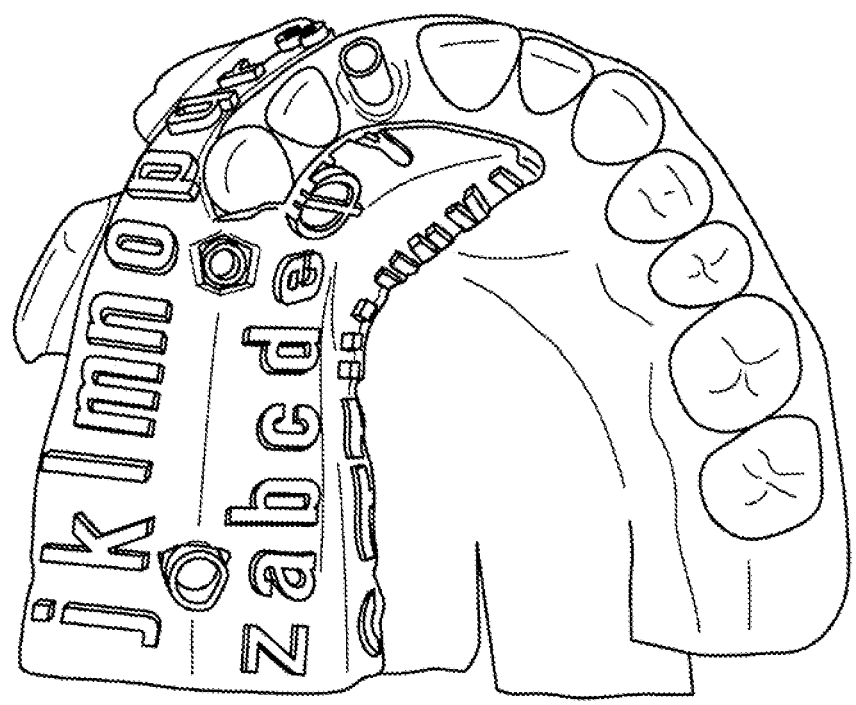
FIG. 13 is a diagram illustrating three-dimensional image data created by the three-dimensional image data creation method using the auxiliary instrument as Example 1.
Figure 14:
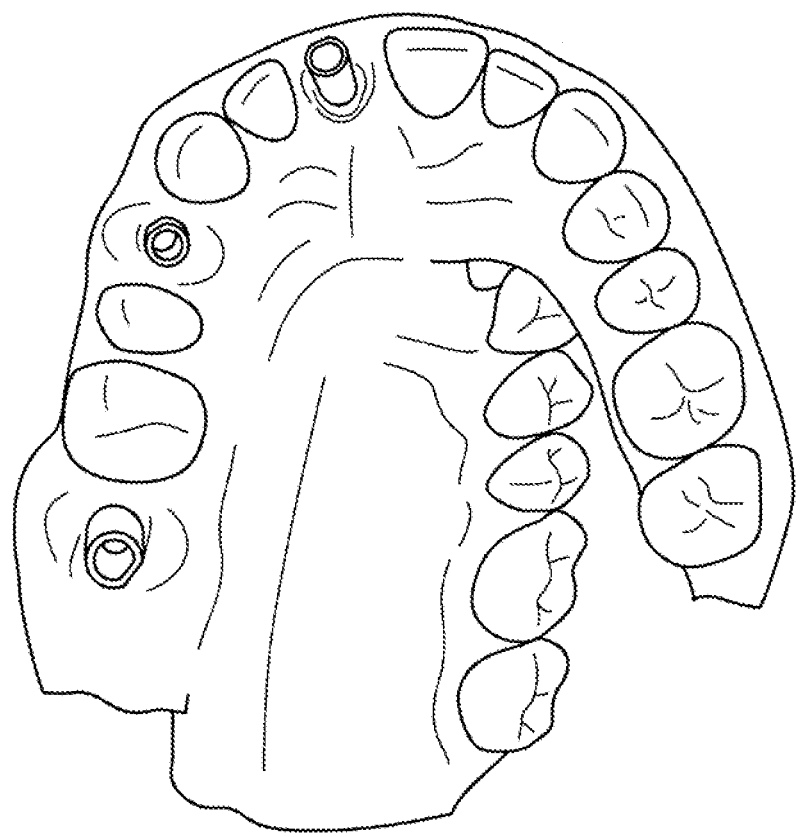
FIG. 14 is a diagram illustrating three-dimensional image data created without using the auxiliary instrument as Comparative Example 1.

FIG. 13 illustrates an example of three-dimensional image data created by the three-dimensional image data creation method using the auxiliary instrument 10 as Example 1. FIG. 14 illustrates an example of three-dimensional image data created without using the auxiliary instrument 10 as Comparative Example 1.

In Example 1, as illustrated in FIG. 13, using the auxiliary instrument 10 connects a plurality of pieces of three-dimensional image data obtained by three-dimensional measuring by the impression taking device by using a plurality of identification portions 12 as an alignment reference. Thus, in Example 1, it is understood that the precision of three-dimensional intraoral image data representing the intraoral shape of the patient is improved.

On the other hand, in Comparative Example 1, as illustrated in FIG. 14, a plurality of pieces of three-dimensional image data obtained by three-dimensional measuring by the impression taking device are connected by using the curvature or the edge of the gingival shape as an alignment reference. Therefore, in Comparative Example 1, there is a case where connection is mistakenly performed when a plurality of pieces of three-dimensional image data are connected together. Therefore, in Comparative Example 1, it is difficult to improve the precision of three-dimensional intraoral image data.

As described above, Example 1 can improve the precision of three-dimensional intraoral image data as compared with Comparative Example 1.

Next, in Example 1 and Comparative Example 1, the distance between the attachment pins 21a and 21b to which the prosthetic device is attached is measured, and respective errors from the actual measured values are calculated.

Figure 15:
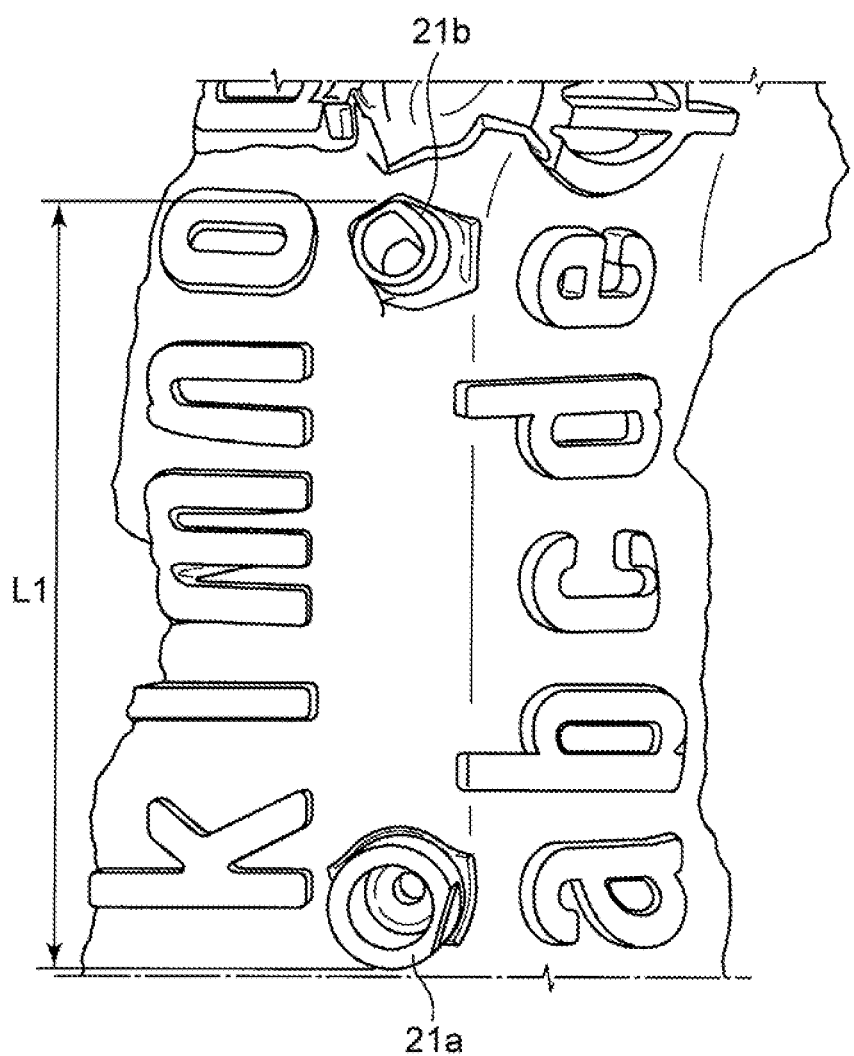
FIG. 15 is a diagram illustrating the distance measured for evaluating the precision of the three-dimensional image data of Example 1.

FIG. 15 illustrates the distance L1 measured for evaluating the precision of the three-dimensional image data of Example 1. Specifically, three-dimensionally measuring three-dimensional image data of Example 1 using an impression taking device (TRIOS3 Oral Scanner, 3Shape) and inputting the obtained data with 3D CAD (Rhinoceros 4.0, version 4.0, Robert McNeel & Associates) measure the distance L1 between the attachment pins 21a and 21b of the three-dimensional image data of Example 1.

In Comparative Example 1 as well, as in Example 1, the distance L1 between the attachment pins 21a and 21b of the three-dimensional image data of Comparative Example 1 is measured by using the impression taking device (TRIOS3 Oral Scanner) and the 3D CAD.

Table 1 illustrates measured values, and measurement results of Example 1 and Comparative Example 1 of the distance L1 between the attachment pins 21a and 21b.

TABLE 1

|  | Distance L1 [mm] | Difference from Measured Value [mm] |
|---|---|---|
| Measured Value | 31.24 | — |
| Example 1 | 31.27 | 0.03 |
| Comparative Example 1 | 31.42 | 0.18 |

As illustrated in Table 1, in Example 1, the difference from the measured value is 0.03 mm. In Comparative Example 1, the difference from the measured value is 0.18 mm. Thus, in Example 1, as compared with in Comparative Example 1, the difference from the measured value decreases, and the precision of three-dimensional image data improves.

Modified Example

Next, an auxiliary instrument of a modified example will be described.

[Auxiliary Instrument]

Figure 16:
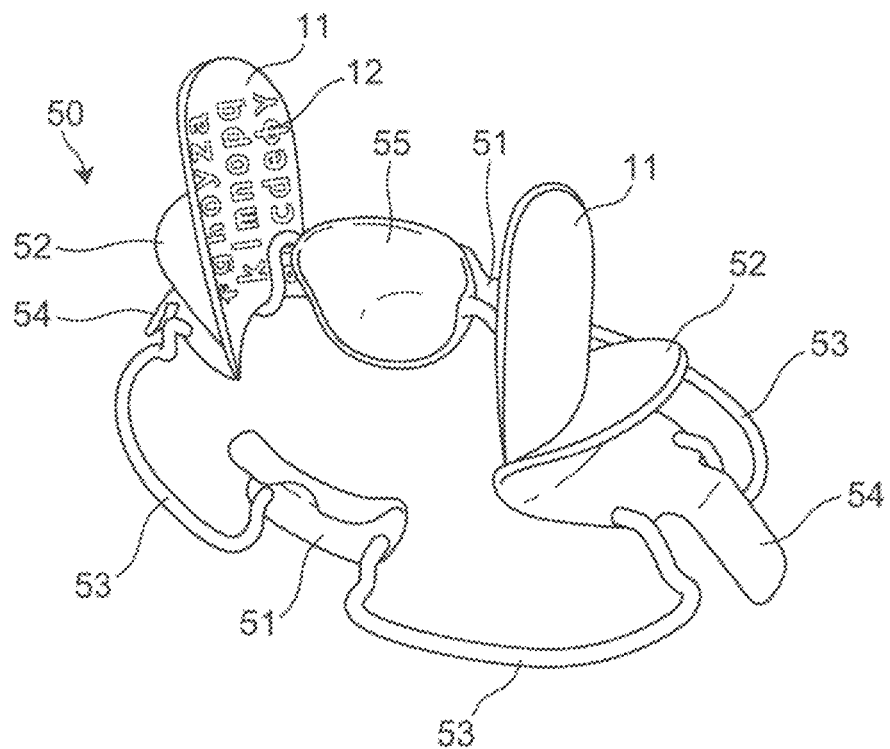
FIG. 16 is a perspective view illustrating an auxiliary instrument of another modified example according to the first embodiment of the present invention.
Figure 17:
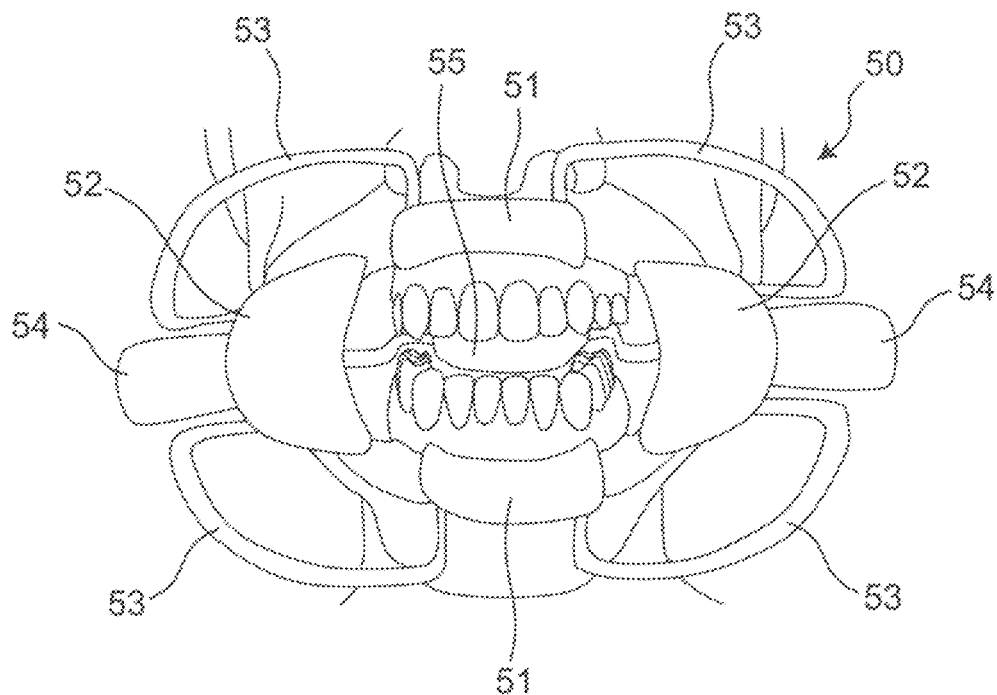
FIG. 17 is a diagram illustrating an example of a state in which an auxiliary instrument of a modified example is attached to the patient's mouth.

FIG. 16 is a perspective view illustrating an auxiliary instrument 50 of another modified example according to the first embodiment of the present invention. FIG. 17 illustrates an example of a state in which the auxiliary instrument 50 is attached to the patient's mouth. The auxiliary instrument 50 illustrated in FIGS. 16 and 17 is configured to be wearable on the patient's mouth.

As illustrated in FIGS. 16 and 17, in addition to the sheet portion 11 having a plurality of identification portions 12 formed, the auxiliary instrument 50 further includes a lip portion 51, a mouth corner portion 52, a coupling portion 53, a handle portion 54, and a tongue fixing portion 55. The sheet portion 11 is connected to the mouth corner portion 52 and extends from the mouth corner portion 52 toward the inside of the oral cavity of the patient. It should be noted that the tongue fixing portion 55 is not indispensable.

The lip portion 51 is a member for spreading and fixing the patient's lips. The respective lip portions 51 are disposed on the patient's upper lip and lower lip. The lip portions 51 widen the upper lip of the patient upward and widen the lower lip downward to expose the gingival portion of the patient. The lip portions 51 have a shape to fit the patient's lips. Specifically, the lip portion 51 has a cross section formed in a recessed shape.

The mouth corner portion 52 is a member disposed at the mouth corner of the patient, that is, at the joint portion between the upper lip and the lower lip of the patient. The mouth corner portions 52 widen and fix the mouth corners of the patient in the left-right direction. The mouth corner portion 52 has a hook shape to fit the mouth corner of the patient. Specifically, the mouth corner portion 52 has a cross section formed in a recessed shape. The mouth corner portion 52 is coupled by the coupling portion 53.

The sheet portion 11 is connected to the mouth corner portion 52. The sheet portion 11 extends from the mouth corner portion 52 toward the inside of the oral cavity of the patient.

The coupling portion 53 is a member for coupling the lip portion 51 and the mouth corner portion 52. The coupling portion 53 is formed of a deformable member. For example, when the lip portions 51 and the mouth corner portions 52 widen the lips and mouth corners of the patient, the coupling portion 53 is deformed. Then, the coupling portion 53 fixes the positions of the lip portion 51 and mouth corner portion 52 by maintaining the deformed state. This allows the patient's mouth to remain open.

The handle portion 54 is a portion that the user can grasp. The handle portion 54 is connected to the mouth corner portion 52 and is formed of a plate-shaped member extending in a direction of widening the mouth corner of the patient from the mouth corner portion 52.

The tongue fixing portion 55 fixes the tongue of the patient. The tongue fixing portion 55 is coupled to the mouth corner portion 52.

Figure 18:
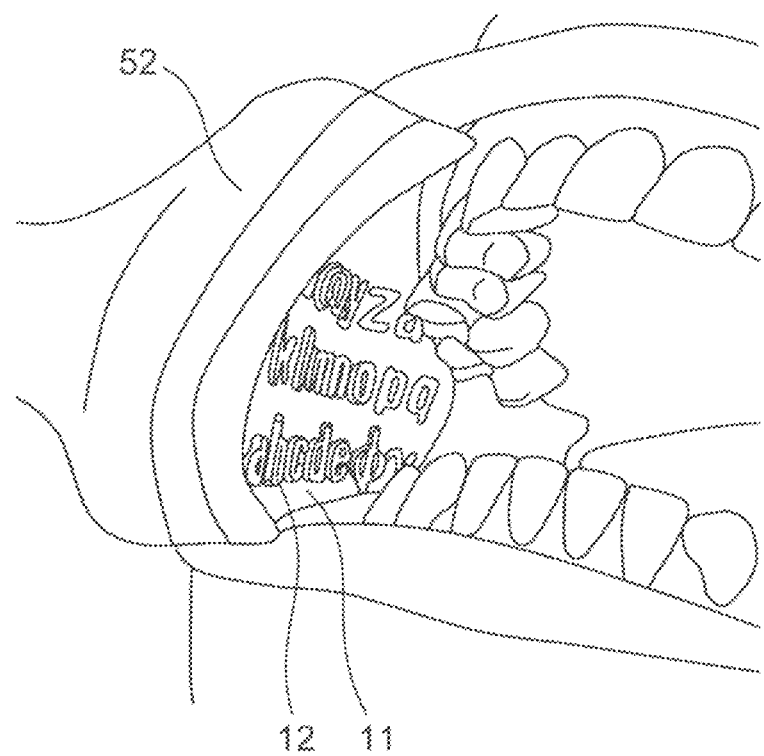
FIG. 18 is a diagram illustrating another example of a state in which an auxiliary instrument of a modified example is attached to the patient's mouth.

FIG. 18 illustrates another example of a state in which the auxiliary instrument 50 is attached to the patient's mouth. It should be noted that in FIG. 18, illustration of the tongue fixing portion 55 is omitted. As illustrated in FIG. 18, in a state where the auxiliary instrument 50 is attached to the mouth of the patient, the sheet portion 11 extending from the mouth corner portion 52 toward the inside of the oral cavity of the patient is disposed in the oral cavity of the patient. Thus, when the three-dimensional measurement of the inside of the oral cavity is performed by the impression taking device, a plurality of identification portions 12 formed on the sheet portion 11 are three-dimensionally measured together with the shape in the oral cavity. As a result, a plurality of pieces of three-dimensional image data can be aligned based on the plurality of identification portions 12 in the auxiliary instrument 50, and the precision of three-dimensional intraoral image data can be improved.

Regarding the manufacturing method of the auxiliary instrument 50, the auxiliary instrument 50 can be manufactured by the same method as the above-described manufacturing method of the auxiliary instrument 10. For example, the auxiliary instrument 50 can be manufactured by injection molding or a 3D printer as described above.

It should be noted that in the auxiliary instrument 50 illustrated in FIGS. 16 to 18, an example in which the sheet portion 11 is connected to the mouth corner portion 52 is described, but the present invention is not limited thereto. The sheet portion 11 may be connected to the lip portion 51 and may extend from the lip portion 51 toward the inside of the oral cavity of the patient.

Figure 19:
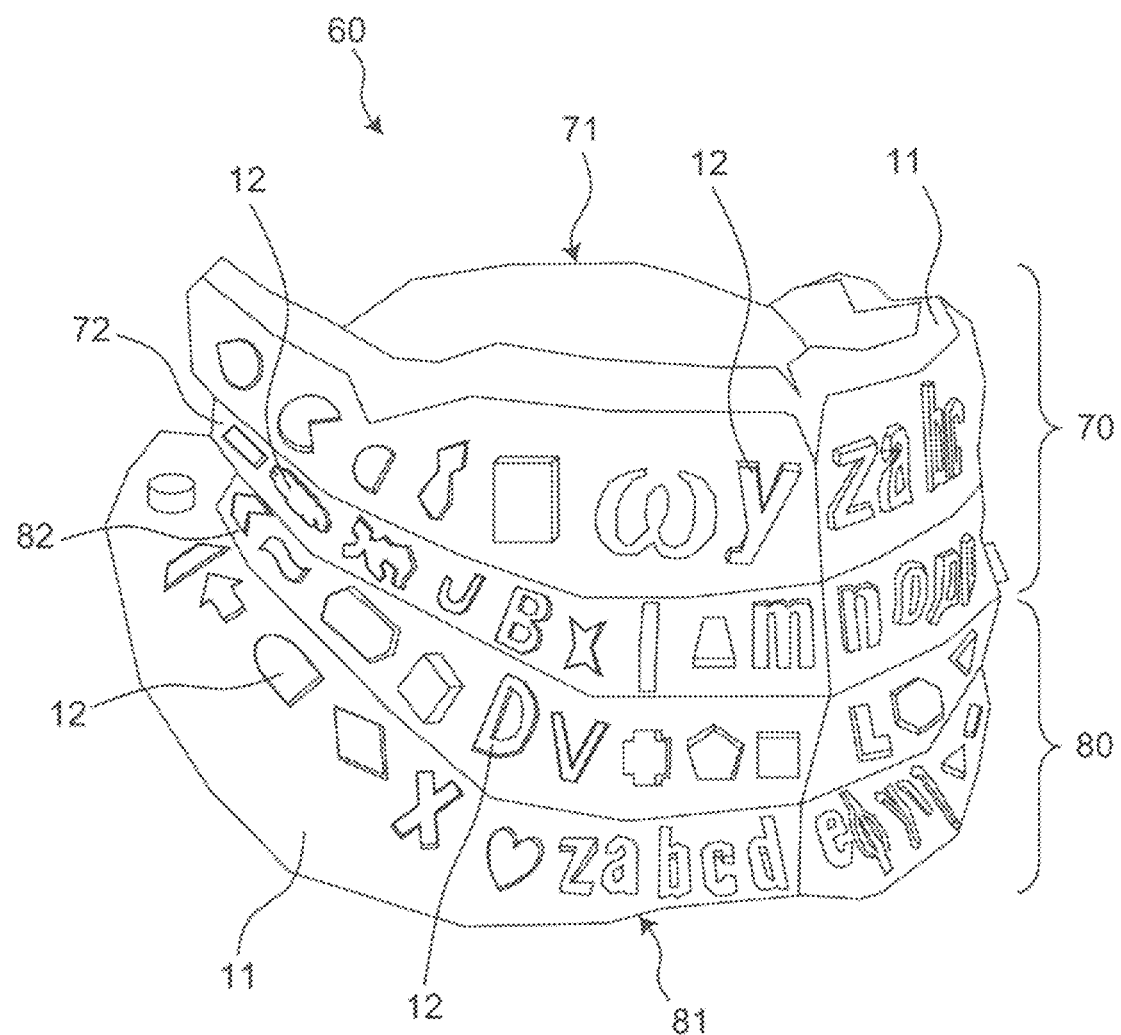
FIG. 19 is a perspective view illustrating another modified example of the auxiliary instrument according to the first embodiment of the present invention.

FIG. 19 is a perspective view illustrating an auxiliary instrument 60 of another modified example according to the first embodiment of the present invention. The auxiliary instrument 60 illustrated in FIG. 19 has a biteplate shape. It should be noted that the auxiliary instrument 60 illustrated in FIG. 19 is used in the case of upper and lower edentulous jaws.

Specifically, the auxiliary instrument 60 includes an upper jaw biteplate 70 and a lower jaw biteplate 80 conforming to the upper jaw biteplate 70. In the embodiment, the upper jaw biteplate 70 and the lower jaw biteplate 80 are not integrally formed and can be separated.

The upper jaw biteplate 70 includes a first base plate portion 71 and a first bite rim portion 72 connected to the first base plate portion 71.

The first base plate portion 71 has a form adapted to the form of the oral mucosa of the patient's upper jaw. Specifically, the first base plate portion 71 includes a first plate conforming to the form of the oral mucosa of the patient's upper jaw and a sheet portion 11, in which a plurality of identification portions 12 are formed, extending from the end face of the first plate toward the oral mucosa of the patient's upper jaw.

The first plate is formed of a semicircular plate-shaped member. The upper surface of the first plate is in contact with the oral mucosa of the patient's upper jaw. The lower surface of the first plate is connected to the first bite rim portion 72.

The sheet portion 11 of the first base plate portion 71 extends from the end face of the first plate toward the oral mucosa of the patient's upper jaw. The end face of the first plate means a side surface connecting the upper surface and the lower surface on the outer surface of the first plate. The end face of the first plate extends in a direction intersecting with the upper surface and the lower surface of the first plate.

The sheet portion 11 of the first base plate portion 71 is formed in a U shape as seen from the upper side of the first base plate portion 71. In a state in which the auxiliary instrument 60 is disposed in the oral cavity of the patient, the sheet portion 11 of the first base plate portion 71 is disposed between the lip and the alveolar crest of the patient.

The first base plate portion 71 is formed of, for example, wax, autopolymer resin (PMMA), or the like.

The first bite rim portion 72 is disposed on the alveolus crest of the upper jaw and is connected to the first plate of the first base plate portion 71. The first bite rim portion 72 is formed of a plate-shaped member. Specifically, the first bite rim portion 72 is formed of a semicircular plate-shaped member. The first bite rim portion 72 extends in the same direction as the extending direction of the first plate of the first base plate portion 71. The upper surface of the first bite rim portion 72 is connected to the lower surface of the first plate of the first base plate portion 71.

On the end face of the first bite rim portion 72, a plurality of identification portions 12 are formed. The end face of the first bite rim portion 72 means a side surface connecting the upper surface and the lower surface on the outer surface of the first bite rim portion 72. In the first embodiment, the first bite rim portion 72 is formed along the shape of the first base plate portion 71.

The first bite rim portion 72 is formed of wax, for example.

The lower jaw biteplate 80 includes a second base plate portion 81 and a second bite rim portion 82 connected to the second base plate portion 81.

The second base plate portion 81 has a form conforming to the form of the oral mucosa of the patient's lower jaw. Specifically, the second base plate portion 81 includes a second plate conforming to the form of the oral mucosa of the patient's lower jaw and a sheet portion 11, in which a plurality of identification portions 12 are formed, extending from the end face of the second plate toward the oral mucosa of the patient's lower jaw.

The second plate is formed of a U-shaped member. The lower surface of the second plate is in contact with the oral mucosa of the patient's lower jaw. The upper surface of the second plate is connected to the second bite rim portion 82.

The sheet portion 11 of the second base plate portion 81 extends from the end face of the second plate toward the oral mucosa of the patient's lower jaw. The end face of the second plate means a side surface connecting the upper surface and the lower surface on the outer surface of the second plate. The end face of the second plate extends in a direction intersecting with the upper surface and the lower surface of the second plate.

The sheet portion 11 of the second base plate portion 81 is formed in a U shape as seen from the lower side of the second base plate portion 81. In a state in which the auxiliary instrument 60 is disposed in the oral cavity of the patient, the sheet portion 11 of the second base plate portion 81 is disposed between the lip and the alveolar crest of the patient.

The second base plate portion 81 is formed of, for example, wax, autopolymer resin (PMMA), or the like.

The second bite rim portion 82 is disposed on the alveolus crest of the lower jaw and is connected to the second plate of the second base plate portion 81. The second bite rim portion 82 is formed of a plate-shaped member. Specifically, the second bite rim portion 82 is formed of a U-shaped member. The second bite rim portion 82 extends in the same direction as the extending direction of the second plate of the second base plate portion 81. The lower surface of the second bite rim portion 82 is connected to the upper surface of the second plate of the second base plate portion 81.

On the end face of the second bite rim portion 82, a plurality of identification portions 12 are formed. The end face of the second bite rim portion 82 means a side surface connecting the upper surface and the lower surface on the outer surface of the second bite rim portion 82. The first bite rim portion 72 is formed along the shape of the second base plate portion 81.

The second bite rim portion 82 is formed of wax, for example.

The auxiliary instrument 60 having the above-described configuration is used for digital bite taking. It should be noted that the auxiliary instrument 60 illustrated in FIG. 19 is an example of a shape used in the case of the upper and lower edentulous jaws. The auxiliary instrument 60 may have a different shape depending on the shape of the residual teeth and the residual ridge mucosa. For example, when bite taking is performed on a patient with remaining teeth, the auxiliary instrument 60 may have a shape in which a hole exposing the teeth to the outside of the auxiliary instrument 60 is formed without covering the remaining teeth.

Digital bite taking using the auxiliary instrument 60 will be described.

(Process A21)

Each of the upper jaw and the lower jaw is three-dimensionally measured by the impression taking device. Thus, three-dimensional image data of the upper jaw and three-dimensional image data of the lower jaw are acquired.

(Process A22)

The auxiliary instrument 60 is disposed in the oral cavity of the patient. Specifically, the upper jaw biteplate 70 is disposed on the patient's upper jaw and the lower jaw biteplate 80 is disposed on the patient's lower jaw. It should be noted that the auxiliary instrument 60 may have a form to expose a part of the residual ridge mucosa.

(Process A23)

In a state where the patient's mouth is closed, bite taking is performed by the impression taking device. Specifically, the upper jaw and the lower jaw are three-dimensionally measured together with the auxiliary instrument 60 by the impression taking device. Specifically, the upper jaw and lower jaw portions covered with the auxiliary instrument 60 and the portion where the residual ridge mucosa is exposed are collectively three-dimensionally measured.

At this time, determination of the centric occlusal position, occlusal plane, and occlusal vertical dimension, the vestibular side contour, the entry of a reference line for artificial tooth arrangement may be performed using the auxiliary instrument 60.

(Process A24)

Three-dimensional intraoral image data in an occlusal condition is created from a plurality of pieces of three-dimensional image data acquired by bite taking. Three-dimensional intraoral image data in an occlusal condition can be created by performing steps ST33 to ST36 illustrated in FIG. 10.

(Process A25)

The three-dimensional image data of the upper jaw and lower jaw obtained in process 21 and the three-dimensional intraoral image data in the occlusal condition obtained in process 24 are aligned by the iterative closest point method (ICP method), for example.

With the above processes, digital bite taking can be performed.

For example, the auxiliary instrument 60 may be manufactured by a method of fixing with an adhesive or the like the sheet portion 11 including a plurality of identification portions 12 in the biteplate manufactured by a usual method. Acquiring the rough three-dimensional image data in the oral cavity, designing the auxiliary instrument 60 by using the dental 3D CAD, and a 3D printer may manufacture the auxiliary instrument 60. Alternatively, the auxiliary instrument 60 may be manufactured by a method of fixing with an adhesive or the like the sheet portion 11 including a plurality of identification portions 12 on the duplicate dentures. The duplicate dentures mean those obtained by acquiring three-dimensional image data with an optical three-dimensional scanner and 3D printing with a 3D printer, or those manufactured by casting an autopolymer resin into a negative mold of old dentures.

According to the auxiliary instrument 60, precision and accuracy of digital bite taking can be improved.

In the first embodiment, an example in which a plurality of identification portions 12 are formed on the end face of the first bite rim portion 72 of the auxiliary instrument 60 is described, but the present invention is not limited thereto. For example, the sheet portion 11 of the first base plate portion 71 may extend from the end face of the first plate to the end face of the first bite rim portion 72. In addition, an example in which a plurality of identification portions 12 are formed on the end face of the second bite rim portion 82 is described, but the present invention is not limited thereto. For example, the sheet portion 11 of the second base plate portion 81 may extend from the end face of the second plate to the end face of the second bite rim portion 82.

In the first embodiment, an example in which the control device being one computer controls the impression taking device, the CT imaging device, and the manufacturing device is described, but the present invention is not limited thereto. For example, each of the impression taking device, the CT imaging device, and the manufacturing device may have a control device.

In the auxiliary instrument, the manufacturing method of the auxiliary instrument, the three-dimensional image data creation method using the auxiliary instrument, the manufacturing method of prosthetic appliance using the auxiliary instrument, and the dimension determination method using the auxiliary instrument of the above-described first embodiment, components may be added, reduced, divided, and integrated depending on the environment where the instrument or the method is to be applied.

Although the present invention is described with a certain degree of detail in each embodiment, the disclosure content of these embodiments should be changed in details of the configuration, changes in combination and order of elements in each embodiment can be achieved without departing from the scope and spirit of the claimed invention.

The auxiliary instrument, the manufacturing method of the auxiliary instrument, and the three-dimensional image data creation method using the auxiliary instrument according to the present invention can create three-dimensional intraoral image data with high accuracy. Therefore, it is useful for quality improvement and homogenization of devices used for medical and dental treatment such as exploration, diagnosis, and prosthetic devices, orthotic devices, space maintainer, splint and surgery support devices in the dental field.

EXPLANATIONS OF LETTERS OR NUMERALS 10, 10A, 10B auxiliary instrument
11, 11a, 11b sheet portion
12 identification portion
13 outer edge portion
14 central portion
20 model
21a, 21b attachment pin
30 impression taking device
50 auxiliary instrument
51 lip portion
52 mouth corner portion
53 coupling portion
54 handle portion
55 tongue fixing portion
60 auxiliary instrument
70 upper jaw biteplate
71 first base plate portion
72 first bite rim portion
80 lower jaw biteplate
81 second base plate portion
82 second bite rim portion

The invention claimed is:

1. An auxiliary instrument for dental use used as a reference of alignment for creating three-dimensional intraoral image data by connecting a plurality of pieces of three-dimensional image data obtained by three-dimensionally measuring an inside of an oral cavity, the auxiliary instrument comprising:
 a sheet portion having a first surface and a second surface opposed to the first surface;
 a plurality of identification portions formed in a thickness direction of the sheet portion from the first surface of the sheet portion, each of the plurality of identification portions having a three-dimensional shape configured to be identified;
 a lip portion configured to widen and fix a lip of a patient;
 a mouth corner portion coupled to the lip portion by a coupling portion, the mouth corner portion configured to widen and fix a mouth corner of the patient; and
 a handle portion connected to the mouth corner portion, the handle portion configured to be gripped,
 wherein the sheet portion is connected to the lip portion and/or the mouth corner portion and extends from the lip portion and/or the mouth corner portion toward an inside of the oral cavity.

2. The auxiliary instrument according to claim 1, wherein the plurality of identification portions have at least one shape of:
 a protrusion protruding in a direction opposite to a direction from the first surface toward the second surface of the sheet portion;
 a recess recessed from the first surface toward the second surface of the sheet portion; and
 hole that allows communication between the first surface and the second surface of the sheet portion.

3. The auxiliary instrument according to claim 1, wherein shapes of adjacent identification portions of the plurality of identification portions are different.

4. The auxiliary instrument according to claim 1, wherein the plurality of identification portions have at least one shape of letters, numbers, signs, pictures, figures, emblems, patterns, symbols, and forms.

5. The auxiliary instrument according to claim 1, wherein each of the plurality of identification portions is formed to have a dimension of 0.10 mm or more and 3.00 mm or less in a thickness direction of the sheet portion and is formed to have a dimension of 0.10 mm or more and 20.00 mm or less in a longitudinal direction and a lateral direction when viewed in a thickness direction of the sheet portion.

6. The auxiliary instrument according to claim 1, wherein the auxiliary instrument is formed of a material including a coloring agent recognized to have biological safety, the material to which an X-ray contrast medium is added.

7. The auxiliary instrument according to claim 1, wherein the sheet portion has a rectangular shape having a thickness of 0.10 mm or more and 3.00 mm or less and a dimension of 1.00 mm or more and 200.00 mm or less in a longitudinal direction and a lateral direction when viewed in a thickness direction of the sheet portion.

8. The auxiliary instrument according to claim 1,
 wherein the sheet portion has a semicircular shape when viewed in a thickness direction of the sheet portion, and
 wherein an arcuate outer edge portion in the sheet portion is bent from the first surface toward the second surface of the sheet portion.

9. The auxiliary instrument according to claim 8, wherein the sheet portion is formed to be bent in a U shape when viewed in a thickness direction of the sheet portion, and has a recessed cross-sectional shape recessed in a direction from the second surface toward the first surface of the sheet portion in a cross section of the sheet portion cut in a thickness direction.

* * * * *